United States Patent [19]

Eppler et al.

[11] Patent Number: 5,225,543
[45] Date of Patent: Jul. 6, 1993

[54] RECEPTORS METHOD FOR PURIFICATION OF G PROTEIN-LINKED

[75] Inventors: Cecil M. Eppler; Hong-Ming Shieh, both of Langhorne, Pa.; John R. Zysk, Frenchtown; Martin J. Corbett, Pemberton, both of N.J.

[73] Assignee: American Cyanamid Company, Wayne, N.J.

[21] Appl. No.: 677,003

[22] Filed: Mar. 28, 1991

[51] Int. Cl.$^5$ .......................... C07K 3/20; C07K 3/12; C07K 3/18; C07K 3/28
[52] U.S. Cl. ................................. 530/413; 530/395; 530/412; 530/415
[58] Field of Search ............... 530/307, 311, 350, 367, 530/387, 412, 413, 415

[56] References Cited

PUBLICATIONS

K. E. Meier et al., *Biochimica et Biophysica Acta* 761: 257–261 (1983).
R. A. Kohanski et al., *J. of Biological Chemistry* 260: 5014–5025 (Apr. 25, 1985).
S. Knuhtsen et al., *Biochem. J.* 254: 641–647 (1988).
B. Ghebrehiwet et al., *J. of Immunological Methods* 110: 251–260 (1988).
C. Susini et al., *J. of Biological Chemistry* 261: 16738–16743 (Dec. 15, 1986).
D. P. Brennan et al., *J. of Biological Chemistry* 262: 14795–14800 (Oct. 25, 1987).
H. T. He et al., *Proc. Natl. Acad. Sci. USA* 86: 1480–1484 (Mar. 1989).
F. Reyl-Desmars et al., *J. of Biological Chemistry* 264: 18789–18795 (Nov. 5, 1989).
N. Kimura et al., *J. of Biological Chemistry* 264: 7033–7044 (Apr. 25, 1989).
L. Dunbar Lewis et al., *Endocrinology* 121: 486–492 (1987).
M. Zeggari et al., *Eur. J. Biochemistry* 164: 667–673 (1987).
A. G. Gilman, *Cell* 36: 577–579 (Mar. 1984).
Redeuilh, Gerard, et al., "The Use of the Biotinyl Estradiol-Avidin System for the Purification of 'Non--transformed' Estrogen Receptor by Biohormonal Affinity Chromatography", *J. Biol. Chem.*, 260:3996–4002, 1985.
Tatemoto, Kazuhiko, "Isolation and Characterization of Peptide YY (PYY), a Candidate Hormone that Inhibits Pancreatic Exocrine Secretion": Proc. Natl. Acad. 79:2514–2518, 1982.
Hochuli, E., et al., "MW Metal Chelate Adsorbent Selective for Proteins and Peptides Cotnaining Neighboring Histidine Residues", Journal of Chromatography, 411:177–184, 1987.
Hadcock, John R. and Craig C. Malbon, "Regulation of Receptor Expression by Agonists: Transcriptional and Post-Transcriptional Controls", *TINS* 14:242–247, 1991.
Helenius, Ari and Kai Simons "Solubilization of Membranes by Detergents", *Bioch. et Biophys. Acta,* 415:29–79, 1975.
Jones, Owen T., et al., "Solubilization and Reconstitution of Membrane Proteins. Biological Membranes:" *A Practical Approach*, J. B. C. Findlay & W. H. Evans, eds., IRL press, Oxford, Washington D.C., pp. 139–178, 1987.
Weinstock, G. M., et al., "Open Reading Frame Expression Vectors: A General Method for Antigen Production in Escherichia Coli Using Protein Fusions to β-Galactosidase" *Proc. Natl. Acad. Sci.* 80:4432–4436, 1983.
Fishman et al., Purification and Characterization of the Rat Liver Vasopressin (VI) Receptor, *J. Biol. Chem.* 262: 14049–14055, Oct. 15, 1987.

*Primary Examiner*—Robert A. Wax
*Assistant Examiner*—Stephen Walsh
*Attorney, Agent, or Firm*—Karen A. Lowney

[57] ABSTRACT

The receptor:ligand complex is applied to a solid phase substrate which binds the complex by specifically binding the ligand. The receptor is dissociated from the substrate bound receptor:ligand complex with an eluant capable of releasing the receptor from the ligand and leaving the ligand bound to the solid phase substrate. GTP containing eluants are effective. The receptor is recovered from the eluate and optionally subjected to further purification.

20 Claims, 12 Drawing Sheets

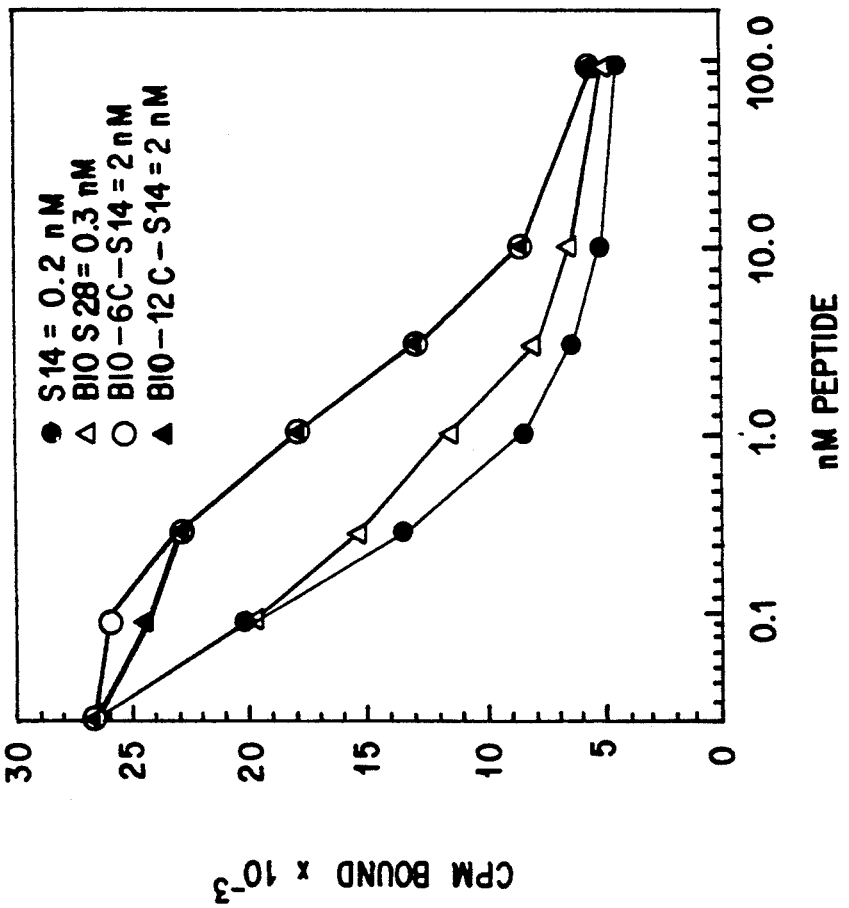

CONC. OF BIO S28 (nM)
FIG. 10B(1)
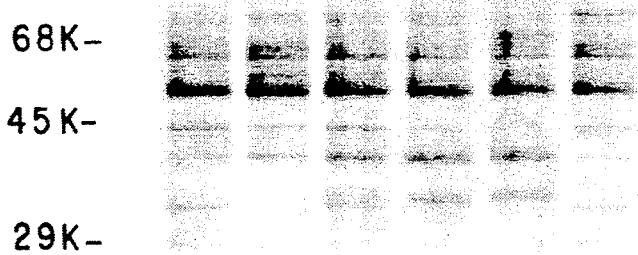
• = G$_i$ ALPHA
FIG. 10B(2)

RECEPTORS METHOD FOR PURIFICATION OF G PROTEIN-LINKED

All animals, both vertebrates and invertebrates, produce a variety of factors including hormones, neurotransmitters, growth factors and other circulating, physiological mediators which are responsible for a wide variety of effects. These include stimulation or inhibition of: protein synthesis, cell division, growth, neural transmission, tissue repair and maintenance, nutrient storage/release and storage/release of other hormones or neurotransmitters. While these factors may be either peptide or non-peptide compounds, they share the common feature of being manufactured and released by cells and exerting their effects through cell surface receptors. Usually the effect is exerted on a different cell (paracrine or endocrine effects) but autocrine effects, whereby a cell secretes a factor that acts on the cell's own surface receptors, also occur. Some of the better known mediators include growth factors (growth hormone or somatotropin, epidermal growth factor, insulin-like growth factors or somatomedins), neurotransmitters (acetylcholine, epinephrine, gamma-amino butyric acid), releasing factors (growth hormone releasing factor, corticotropin releasing factor, somatostatin) and circulating hormones (insulin, glucagon, thyroid hormone). Some of these compounds, such as insulin, epinephrine and somatostatin fall into more than one category and regulate many different functions.

Each of these factors acts initially by binding to a receptor protein, which may be located either on the surface or in the cytoplasm of the particular factor's target cell. The receptor has a binding site which has a high affinity and specificity for the growth factor or hormone; when the binding between factor and receptor occurs, a sequence of reactions is initiated which in some manner alters the functioning of the target cell. For example, it may cause the target cell to increase production and secretion of a particular protein, or alternately, it may signal the target cell to temporarily cease or decrease production of a certain protein.

Identification and purification of receptor proteins has become an important focus in molecular biology in recent years. Manipulation of receptor function is one way in which the action of the signalling compound can be modulated. For example, if in a given situation the ultimate effect of a hormone or growth factor is undesirable, blocking or otherwise interfering with receptor binding will prevent this action. Similarly, there are situations in which it may be desirable to increase the numbers of receptor sites in certain cell types or to place a specific receptor in a cell type which had not previously expressed it. The ability to manipulate the receptor binding, however, is dependent as much upon initial purification of the receptor and definite confirmation of its identity, as it is dependent upon knowledge of the details of the structure of the purified receptor. Unfortunately, thorough purification of the receptor is one of the more difficult tasks to accomplish.

This problem is particularly difficult when the receptor to be purified is one which is associated with GTP-binding regulatory proteins (hereafter referred to as G proteins). Each of the various G proteins consists of three structurally distinct subunits designated alpha, beta and gamma. Because structural variants exist for each G protein subunit, a large variety of different G proteins exists. The G proteins function to couple their associated receptor to cellular effector systems such as adenylate cyclase (Gilman, Ann. Rev. Biochem 56: 615-649, 1987), ion conductance channels (Birnbaumer et al., Biol. of Reproduction 44: 207-224, 1991) and polyphosphoinositide-specific phospholipase C (Smroka et al., Science 251: 804-807, 1991). G protein associated receptors can bind their corresponding hormone, neurotransmitter or other mediator (hereafter, referred to as "ligands") with low affinity in the absence of G protein. However, high affinity binding requires an intact tetrameric complex of receptor +G protein. An exception to this rule is the binding of antagonists. Antagonists are non-physiological, "blocking" ligands, often used as drugs, which occupy a receptor's binding site but do not activate the G protein-dependent signalling mechanisms. Antagonists bind their receptors with the same affinity in the presence or absence of G proteins (Stadel and Lefkowitz, Endocrinology, 2nd Ed., Vol. 1: 75-93, 1989. L. J. DeGroot, ed., W. B. Saunders Co.).

Isolation of receptors primarily depends on exploitation of the receptor's affinity for a particular ligand. If an antagonist is not available or is not effective for the purification of a particular G protein-linked receptor, the tetrameric structure must be substantially maintained throughout most of the purification procedure. This consideration is particularly relevant to the purification of peptide receptors, for which antagonists are difficult to obtain.

Although individual details vary, the classical approach to such receptor isolation is to solubilize cell membranes containing the ligand-free receptor and to pass the solubilized material, containing the receptor, through an affinity column containing immobilized, receptor-specific ligand. After binding, the putative receptor is eluted from the column. This approach may have several drawbacks, depending on the receptor. First, it requires that a binding assay be developed for the solubilized receptor. Also, many solubilization processes dissociate G proteins from receptors. For example it is claimed that the plant glycoside digitonin is the only detergent that allows solubilization of adrenergic receptors in active form (Caron and Lefkowitz, J. Biol. Chem. 251: 2374-3484, 1976). Digitonin is also said to be the preferred detergent for solubilization of the vasoactive intestinal peptide receptor from lung (Patthi et al., J. Biol. Chem. 263: 19363-19369, 1988). Also, some receptors such as the pituitary somatostatin receptor will not, in our experience, readily bind ligand after solubilization. This makes the use of a traditional affinity column untenable. In fact, as detailed below, both traditional affinity chromatography and immunopurification of "solubilized somatostatin receptors" have given highly ambiguous results.

Previous efforts directed toward purification of SRIF (somatotropin release inhibitory factor or somatostatin) receptors have yielded ambiguous or incomplete results. Some investigators have reported solubilization of SRIF receptor: [$^{125}$I]SRIF complexes (Zeggari et al., Eur. J. Biochem. 164: 667-673, 1987; Knuhtsen et al., Biochem. J. 254: 641-647, 1988) and even high affinity, free SRIF receptor (Knuhtsen et al., J. Biol. Chem. 265: 1129-1133) from pancreatic acinar membranes. The solubilized receptor:ligand complexes and solubilized free receptor could both be partially separated from other proteins by gel filtration and by wheat germ agglutinin binding (via oligosaccharide residues). Both of these methods are too crude to give significant purification of receptors. There have been no reports of pancreatic SRIF receptor purification by affinity chromatography. He et al. (Med. Pharmacol. 37: 614–621, 1990) reported solubilization of high-affinity, brain SRIF receptor and also purification of the solubilized brain receptor on immobilized D-Trp8-SRIF14 (PNAS USA 86: 1480–1484). However, no SRIF binding activity was reported for the affinity column eluates. Instead, an [$^{125}$I]-labelled SRIF analog was chemically cross-linked to a 60,000 MW protein in the eluate. This was presumed to be a low affinity, monomeric form of the SRIF receptor. Purification of the human gut SRIF receptor from the HGT-1 cell line was reported by Reyl-Desmars et al. (J. Biol. Chem. 264: 18789–18795, 1989). In this work, somatostatin binding activity was seen in a preparation obtained from solubilized membranes via sequential binding to affinity columns made with an alleged (but poorly characterized) anti-SRIF receptor antibody and with somatostatin. The purified fraction contained primarily one band (MW 90,000) and showed lowered SRIF binding affinity consistent with uncoupling from G protein. The 90 k band was unusual for a membrane receptor in that it was a narrow, sharply focused band after SDS polyacrylamide gel electrophoresis. Most receptors contain substantial amounts of covalently bound oligosaccharide, which gives them a poorly focused, "fuzzy" appearance on gels.

It is apparent, as shown above, that prior attempts to purify SRIF receptors have suffered from loss of binding affinity due to dissociation of receptor-G protein complexes. This compromises positive identification of the receptor. Lack of a positive identification of the receptor, lack of enough pure material for sequencing, or simply the inadvertent isolation of a non-receptor protein probably accounts for the fact that neither of the receptor preparations mentioned above has led to a definitively purified somatotropin receptor. Similar problems exist in the purification of other G protein-linked receptors. For example, the receptors for angiotensin II (Marie et al., Biochemistry 29: 8943–8950, 1990), luteinizing hormone, releasing hormone (LHRH; Ogier et al., J. Endocrinol. 115:151–159, 1987) and parathyroid hormone (Brennan and Levine, J. Biol. Chem. 262-14795–14800, 1987) have been extremely difficult to solubilize in active form. With this problem in mind, Marie et al. (ibid), Brennan and Levine (ibid) and Ogier et al. (Biochem. J. 258: 881–888, 1989) developed purification strategies that utilized biotinylated peptides and purification of receptor:ligand complexes on streptavidin columns.

Many investigators have turned to biotinylated ligands for the purification of difficult receptors. This method employs the strong affinity between biotin and the biotin binding proteins avidin and streptavidin to purify receptor:biotinyl-ligand complexes (Hoffman and Kiso, PNAS USA 73: 3516–3518, 1976). Typically, the receptor is one that has resisted purification by traditional affinity methods. Receptors approached by this method include angiotensin II (Marie et al., ibid), parathyroid hormone (Brennan and Levine, ibid), adrenocorticotropic hormone (Hofmann et al., Biochemistry 25: 1339–1346, 1986), beta-endorphin (i.e., mu and delta opioid receptors; Hochhaus et al., J. Biol. Chem. 263: 92–97, 1988) gonadotropin releasing hormone (Hazum et al., J. Biol. Chem. 261: 13043–13048, 1986), dynorphin (i.e. kappa opioid receptor; Goldstein et al., PNAS USA 85: 7375–7379, 1988) and luteinizing hormone releasing hormone (Ogier et al., ibid). It is important to note that all of these receptors are G protein-linked. None of the above methods yielded clearly identified, pure receptor. Some of them, for example Marie et al. (ibid), Brennan and Levine (ibid), Hazum et al. (ibid) and Ogier et al. (ibid) purified the supposedly identified receptors indirectly after chemical cross-linking to the biotinylated ligands. This method cannot detect contaminating proteins and provides inadequate functional correlates (such as high affinity ligand binding) for the purified proteins.

Clearly, a reliable method for G protein-linked receptor purification is needed to provide receptors in adequate quantities and in sufficiently pure and intact condition to permit sequencing. The biotinylated ligand approach, while attractive, needs development to make it applicable for generating pure, sequencable quantities of receptor.

SUMMARY OF THE INVENTION

The present invention provides a method for purification of cellular receptors. In particular, the method is useful for purifying receptors associated with G proteins. The method comprises the steps of contacting a receptor-specific ligand with cellular material containing the receptor to form a receptor:ligand complex; solubilizing the complex; contacting the solubilized complex with a substrate which binds the receptor:ligand complex; and contacting the bound receptor:ligand complex with an eluant which releases the receptor from the ligand and into the eluate. In a preferred embodiment the eluant also releases the receptor from its associated G proteins which are also released into the eluate. Two particularly preferred embodiments are: 1. the ligand is biotinylated and the substrate to which the receptor:ligand complex is bound contains avidin or streptavidin and 2. the purification protocol can be adapted as a semi-quantitative assay to positively identify the receptor protein.

There are several advantages to the present method as applied to G protein linked receptors. It overcomes the problems encountered with receptors that lose ligand binding capacity on solubilization, by prebinding the ligand to the receptor before solubilization. Prebinding, followed by complex solubilization, also circumvents the need for developing a binding assay for the solubilized receptor. The use of prebound biotinylated ligands exploits the strong affinity of biotin for streptavidin, enhancing the potential recovery of the receptor, and avoids the need to rely on the receptor's binding capacity which may be compromised after solubilization if not previously ligand-bound. The method also retains the integrity of the tetramer until the final elution step and, in a preferred embodiment provides for the elution of G protein along with the receptor. The retention of G protein not only aids in maintaining stability of the receptor:ligand complex during purification but also provides a confirmation in the final stage of isolation that the principal protein purified is in fact the receptor. The final affinity column eluate contains a substantially pure receptor, depleted of the cellular proteins normally found associated with the membrane and also contains the specific, receptor-associated G protein subunits. This provides a confirmation of the identity of the purified protein as a true receptor and also allows subsequent identification of the exact G protein subspecies associated with a given receptor.

The present invention also encompasses receptors isolated by the claimed method.

DETAILED DESCRIPTION OF THE INVENTION

Figure 1:
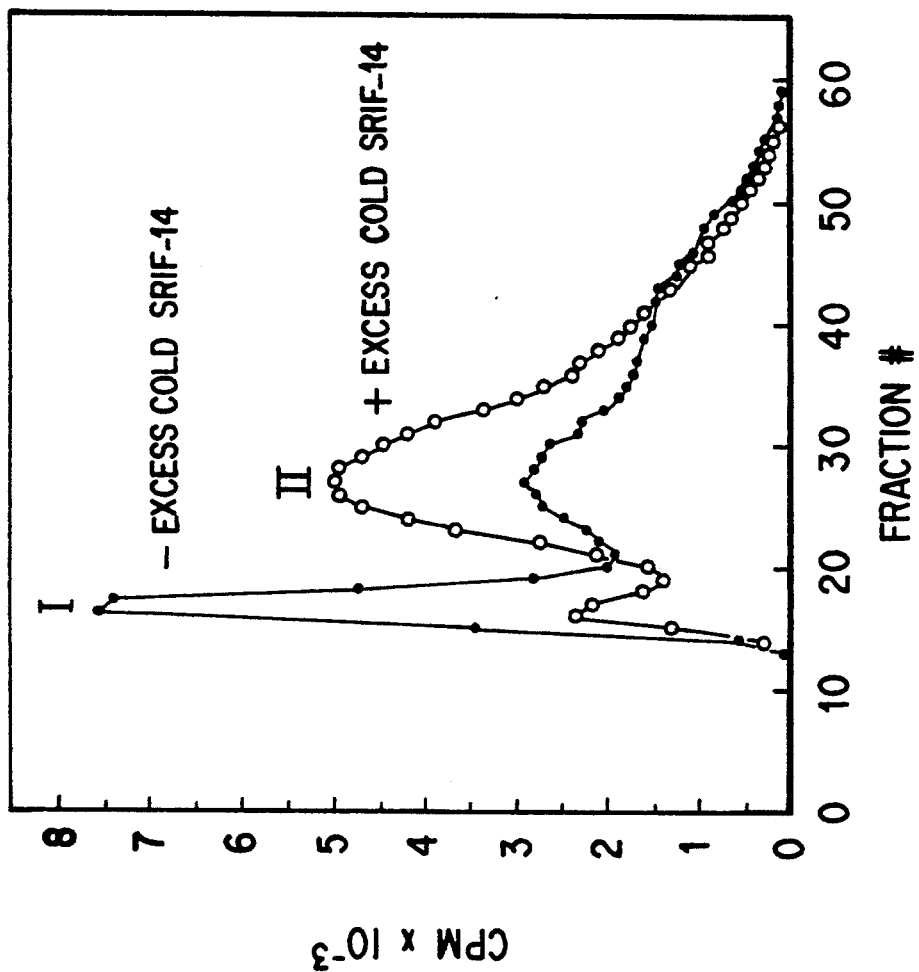
FIG. 1 illustrates separation of receptor-bound and free [$^{125}$I]Tyr11-S14. Radioligand is bound to GH$_4$C$_1$ membranes as described in "Materials and Methods". The binding incubations contain 2 mg membrane protein and $6 \times 10^6$ cpm of radioligand in 8 ml. A non-specific binding sample is identical except for the addition of 1 uM cold S14. Initial cpm bound were $1.43 \times 10^6$ (total) and $0.65 \times 10^6$ (non-specific). After the binding step, membranes are resuspended at 1 membrane protein per ml in the presence of 1% CHAPS detergent in a buffer containing 25 mM Tris (pH 8), 10% glycerol and 0.2 mM CaCl$_2$ (solubilization buffer). A protease inhibitor cocktail ("$100 \times 4$ pase" described in "Materials and Methods") is also added as 1% of final volume. Solubilization is allowed to proceed for 1 hour on ice, and then the mixture is centrifuged for 30 minutes at $100,000 \times g$. CPM in the $100,000 \times g$ supernatant were $0.61 \times 10^6$ (total) and $0.29 \times 10^6$ (non-specific). Free [$^{125}$I]Tyr11-S14 is added to the non-specific binding sample to give equal cpm in the two samples. Then 0.25 ml aliquots of each supernatant (95–90,000 cpm) are loaded onto $0.8 \times 13$ cm columns of Sephadex G-50. The columns are eluted at a flow rate of 0.7 ml/min with solubilization buffer + 1% BSA. 0.18 ml fractions are collected and counted for radioactivity.

The present method is applicable to isolation of any type of receptor. However, it is a particular advantage in purifying any receptor which is in situ, naturally associated with G proteins. The receptors may be either of the stimulatory or inhibitory type, and include, but are not limited to receptors for vasoactive intestinal peptide, growth hormone releasing factor, angiotensin, somatostatin, opioids, adrenocorticotropic hormone, corticotropin releasing factor, gonadotropin releasing factor, vasopressin/oxytocin, glucagon, cholecystokinin, parathyroid hormone, calcitonin, calcitonin gene related peptide, neuropeptide Y, peptide YY, secretin, gelanin, kyotorphin, peptide histidine isoleucine, bradykinin, neurotensin, prostaglandins (E1, E2, D, I$_2$ and F$_2$-alpha), leukotrienes (A$_4$, B$_4$, and C$_4$), thrombin, phosphatidic acid, platelet activating factor, thromboxane, leukotrienes, serotonin (5HT 1b, 2 and D), histamine, gamma amino butyric acid, glutamic acid, adenosine (A1 and A2), purines (P1, P2t, P2x and P2y), novel insect neuroactive compounds such as N-beta-alanyl-dopamine and various chemoattractant, light, taste and odor receptors. The method is particularly advantageous in the purification of the somatostatin receptor, and in purification of receptors which, like the SRIF receptor, interact with ion channels (K$^+$ and Ca$^{2+}$) and/or with adenylate cyclase in an inhibitory manner. This includes receptors for adenosine (A1), adrenaline (alpha$_{2b}$), angiotensin, gamma amino butyric acid (GABA$_b$), serotonin (5HT$_{1B}$ and 5HT$_{1D}$), neuropeptide Y, neurotensin, opioids (mu, delta, kappa), prostaglandins (E1, E2 and E2) and purines (P2t).

The purification is typically initiated with a crude membrane preparation of the cell type containing the receptor. Although no single procedure can be considered optimal for all tissues, one important, general consideration is to minimize the levels of GTP in the final membrane preparation. It is generally known that addition of the metal ion chelators EDTA and EGTA to media for membrane preparation will cause dissociation of GTP from G proteins and increase ligand binding affinity of G protein-linked receptors. It is preferred that the cell line chosen expresses the receptor at a high level, e.g., at least about 0.3 pmoles/mg of membrane protein. The binding affinity of the receptor should preferably be about 1 nM kd. Unlike many previous methods, which first solubilize the unbound receptor, the present method first contacts the receptor with the ligand to be used, before solubilization. The ligand chosen will depend upon the identity of the receptor to be isolated, and will be selected for its specificity and affinity for the target receptor. It may be the naturally occurring ligand from the receptor, or an analogue thereof with the equivalent or superior affinity for the receptor. Preferably, the ligand will be detectably labelled, usually radiolabelled. Radiolabeled analogues of various ligands, such as somatostatin or VIP can be routinely prepared using methods known in the art.

In a preferred embodiment, the ligand is biotinylated. Biotinylation is employed in connection with the preferred method of affinity chromatography, wherein the ligand:receptor complex is isolated by contact with an avidin- or streptavidin-containing substrate. Biotinylation techniques are known in the art (Pierce Chemical Co. ImmunoTechnology Handbook and Catalog, Vol. 1:D2-D46, 1990). Thus, in addition to having high affinity for the receptor, the chosen ligand should also have good biotinylation characteristics, i.e., it can be readily biotinylated without interfering with its receptor binding. This may be possible by virtue of the ligand being relatively large, with biological activity (i.e., binding ability) localized at or near one end of the molecule so that the other end can be routinely modified without affecting its activity. Certain peptide ligands such as SRIF28 and beta-endorphin (Hochhaus et al., ibid) exemplify this characteristic. In some cases, it may be desirable to add a spacer between the nonactive portion of the molecule and the biotin to reduce the possibility of interference with the ligand's binding capacity, and to also enhance the availability of the biotin for binding to avidin and streptavidin. Exploitation of the very high affinity between avidin (or streptavidin) and biotin for receptor isolation gives the potential for a single, high-yield (20–70%), high-purification, affinity step in which a receptor:biotinyl-ligand complex binds to a column of immobilized avidin or streptavidin. Elution, either by dissociation of the receptor from ligand or of the ligand from avidin/streptavidin, should yield an identifiable, purified or semi-purified receptor. The selection of avidin/streptavidin:biotin interactions for receptor isolation offers unique advantages. This method provides a routine approach to receptor purification; one which, with modifications (different ligands, different receptor source, possibly different detergents) can be used for most G-protein linked receptors. Avidin/streptavidin is ideally suited to such an approach, and is particularly preferred, being relatively cheap and commercially available from many sources (Pierce, Sigma, Vector Labs, etc.) and in a variety of forms (with or without spacers, succinylated, free and immobilized, different isoforms, etc.). Thus an appropriate affinity matrix will almost always be available. Also, prebinding of ligand and solubilization of a receptor:biotinyl-ligand complex from membranes eliminates the need to construct an immobilized ligand affinity matrix and specifies the use of immobilized avidin or streptavidin. However, there are embodiments of this method which use other affinity matrices such as immobilized anti-ligand antibodies. It is important to note that the term "affinity column or substrate" will hereafter be used to denote the initial, ligand binding column or substrate whether it contains immobilized avidin/streptavidin, anti-ligand antibody or any other ligand-binding reagent.

The chosen ligand is incubated with the membrane preparation for a period of time sufficient to allow maximum binding of ligand to all available receptor sites; usually 1–5 hours is sufficient. The membranes are then spun down, washed, and recentrifuged. The supernatant is removed and the preparation is ready for solubilization.

The selection of detergent for solubilization of the receptor:ligand complex can be crucial to the success of the method. The important criteria for detergent selection are (1) it should be able to fully solubilize the complex; (2) it should permit the complex to remain stable in solution, i.e., there should be little or no dissociation of receptor from ligand; (3) it should not interfere with the ability of the complex to bind the affinity column used for purification; in the preferred embodiment of the invention, the detergent should not interfere with the ability of biotin to bind to avidin or streptavidin.

For example, in purification of the somatostatin receptor, it has been found that all detergents are not equally useful for solubilization in this particular method. Many detergents, such as Triton X-100, zwittergent, and lysolecithin adequately solubilize the complex (see Examples, FIGS. 2 and 3); however, their performance in stabilizing and/or noninterference with affinity binding is less than optimal. For example, although CHAPS solubilization produces a reasonably stable intact receptor:ligand complex, the total solubilization of radioligand is relatively low. In contrast, although Triton x-100 gives good solubilization of the bound radioligand, it also produces the greatest dissociation of the receptor:ligand complex.

It is, of course, possible to utilize any detergent which will solubilize, stabilize, and permit affinity binding of the complex to some extent, with attendant suboptimum results and yield. However, because available amounts of receptor are generally in relatively short supply, it is preferred that these three aspects of the invention be maximized to the extent possible by use of the appropriate detergent. A favorable balance of these important features is generally obtained with the use of detergents of the bile-salt type, either natural or synthetic; such detergents include but are not limited to deoxycholate, digitonin and cholate. A particularly good combination is deoxycholate and lysolecithin (a non-bile salt which solubilizes receptor and interacts favorably with deoxycholate), in equal amounts, at a concentration of 0.2% or less, and preferably at about 0.1–0.15%, based on an assumed concentration of membrane protein of 1 mg/ml in the solubilization step. The ratio of detergent to membrane protein may be as important as the absolute concentration of detergent in some cases. It can be seen, by reference to FIG. 3, that although deoxycholate alone is adequately effective, and lysolecithin alone less so, the combination of the two is much more effective than either one of the detergents alone.

Determination of alternate detergents useful in this step, for optimization with other types of receptors, can be made following the procedures outlined in Example II, infra, utilizing the detergent and receptor of choice.

Once the receptor:ligand complex has been solubilized, it is then isolated by affinity chromatography. For the purposes of the present invention, the use of an affinity substrate containing avidin or streptavidin is particularly preferred, in conjunction with the use of biotinylated ligands to bind the receptor. The extraordinary affinity of biotin for avidin or streptavidin permits a very strong and specific binding of the complex to the affinity matrix, thereby enhancing recovery of the solubilized complex. Appropriate matrices for this purpose are readily available commercially (vide supra). Alternate affinity purification methods can be employed, such as use of an anti-ligand antibody capable of binding the receptor:ligand complex; however, this approach may be less reliable in producing adequate quantities of receptor for analytical purposes.

The solubilized complex is combined with the chosen substrate and permitted to bind for several hours. The substrate containing bound receptor is then washed in an appropriate buffer; the flow-through should contain little or no receptor:ligand complex. Elution of the receptor, according to the present method, involves dissociation of the receptor from the ligand, rather than dissociation of the ligand from the affinity substrate. To achieve this end, any eluant which will reverse the binding of the receptor to the ligand is appropriate. In a preferred embodiment of the invention, G protein binding compounds, such as the nonhydrolyzable GTP analogs GTP-gamma-S, or Gpp(NH)p or GTP are used in the concentration range of 1 to 100 uM to dissociate G protein from the receptor, thereby lowering ligand affinity and causing specific elution of the receptor and G protein subunits from the affinity column. In an especially preferred embodiment of the invention, one or more divalent cation chelating agents are employed to facilitate the dissociation. Since both binding of ligands (often) and of G proteins (always) are known to be divalent cation-dependent (usually $Mg^{2+}$ or $Ca^{2+}$), the use of chelating agents can enhance the recovery of receptor from the affinity column. Examples of appropriate chelating agents for this purpose are EDTA and EGTA, either alone or in combination. They should be present in molar concentrations at least equal to that of any divalent cations to be chelated. With EDTA, EGTA and a GTP analog in the elution buffer, the receptor is eluted in a form non-associated with G protein although G protein subunits are also present in the eluate. Preferably, the affinity column would be eluted with 3-5 column volumes of elution buffer to ensure complete recovery of eluted proteins.

In alternate embodiments of the invention, either GTP analogs or EDTA/EGTA are used separately for elution of receptor. It may be possible, for example, to preferentially elute G protein but not receptor by use of GTP analog. It may also prove possible to elute receptor with minimal or no dissociation from G protein by use of chelating agents only in the elution buffer. This approach may be preferably for reconstitution of ligand binding activity in the eluate since it would be unnecessary to remove the GTP analog prior to the demonstration of high affinity ligand binding.

The final purification step or steps are a matter of choice. The receptor as eluted from the affinity column is sufficiently pure for many purposes, including identification of receptor protein on SDS-polyacrylamide gels, radioligand binding studies, characterization and identification of G protein subunits and possibly immunization. Receptor purity should range from 5-25% at this point. However, where the highest possible level of purity is required, it may be desirable to further purify the receptor. Since most of the receptors of interest are glycoproteins, lectin affinity chromatography is a preferred secondary method of receptor clean-up. In particular, binding to wheat germ agglutinin-agarose, followed by elution with N-N'-N"-triacetylchitotriose, is an effective means of further glycoprotein receptor purification. In this case, G proteins will not bind to the column and will appear in the flow-through, while the receptor alone appears in the eluate.

The combination of an affinity column plus a lectin column as described above can yield receptor pure enough for amino acid sequencing. Additional steps such as gel electrophoresis, HPLC and deglycosylation may be used in specific instances. Applications for these techniques are as follows: (1) SDS-PAGE. This may be used for final purification of receptor either after the affinity step or after a lectin binding step done subsequent to an affinity step. SDS-PAGE may also be used for purification of proteolytic fragments derived from the receptor. (2) HPLC (reverse phase, ion exchange or hydrophobic interaction). This may be used instead of SDS-PAGE, for the same purposes as described above. Relative utility of the methods will depend on the protein being purified, and will be apparent to those skilled in the art. Both methods are useful for separation and identification of G protein subunits and could be applied also to deglycosylated forms of the receptor if that proves advantageous. Observation of the presence of G proteins in the eluate serves as confirmation that the main protein isolated is in fact the receptor sought. Further confirmation of the identity of the G proteins can be obtained by ADP-ribosylation catalyzed with cholera toxin (Gill and Meren, PNAS USA 75:3050-3054, 1978; Cassel and Pfeuffer, PNAS USA 75:2669-2673, 1978) or pertussis toxin (Katada and Ui, J. Biol. Chem. 257:7210-7216, 1982; Bokoch et al., J. Biol. Chem. 238:2072-2075, 1983) and immunoblotting (Mumby et al., PNAS USA 83:265-269, 1986).

EXAMPLES

1. GENERAL MATERIALS AND METHODS

Unless otherwise stated, the following are used in the examples provided below:

A. Synthesis of Peptides—Four biotinylated SRIF analogs are synthesized. Two analogs, biotinyl-[NH—(CH$_2$)$_5$—CO]—NH-(Tyr11)SRIF14 (="Bio-6C-S14") and biotinyl-[NH—(CH$_2$)$_5$—CO]$_2$—NH-(Tyr11)SRIF14 (="Bio-12C-S14") are synthesized at Applied Biosystems, Foster City, Calif. Bio-C6-S14 is synthesized on solid phase by the FMOC method. Bio-12C-S14 are synthesized on solid phase by the t-BOC method. The aminocaproate spacers are added by use of BOC-aminocaproate with DCC-HOBT coupling (The Peptides: Analysis, Synthesis Biology, Vol. 1, E. Gross, J. Meinhofer, eds. Academic Press, 1979). The N-terminal biotin is also coupled by DCC-HOBT. Biotinyl-NH-(Leu9, D-Trp22, Tyr25)SRIF28 is synthesized at Peninsula Labs, Belmont, Calif., on solid phase by the t-BOC method. Biotin is coupled to the N-terminal by DCC-HOBT. Biotinyl-NH-SRIF14 is synthesized at American Cyanamid, Agricultural Research Division, Princeton, N.J. This is done on solid phase by the t-BOC method. Biotin is coupled to the N-terminus by DCC-HOBT.

B. Pituitary Cell Culture—GH$_4$C1 rat pituitary tumor cells are initially grown as monolayers in 82.5% Dulbecco's MEM (Gibco)+15% heat inactivated horse serum+2.5% heat inactivated fetal bovine serum (sera from CC Labs, Cleveland, Ohio)+50 units/ml penicillin and 50 ug/ml streptomycin. The cells are then placed in suspension culture by replacement of MEM by suspension culture medium (MEM modified for suspension culture of "S-MEM", Gibco) and culturing in spinner flasks (Bellco, Vineland, N.J.). The concentration of horse serum is gradually reduced to 11% and the medium is supplemented with HEPES buffer and extra glucose. The medium finally developed for optimal growth of the GH$_4$C1 cells in suspension culture is as follows (expressed in % of total volume per liquid component): 84.5% DMEM+11% horse serum+2.5% fetal bovine serum+1% HEPES buffer (pH 7.4; 10 mM final conc.)+1% penicillin/streptomycin solution (5,000 units/ml pen+50 ug/ml strep)+0.7% 45% glucose solution. Cells are grown at 37° C. in the presence of 6% $CO_2$. Cultures are initially seeded at $1.5-2 \times 10^5$ cells/ml and grown to concentrations of $6-10 \times 10^5$ cells/ml (3-4 days growth). Cells are passed by dilution or complete medium change every 3-4 days. Viability is greater than 95% by trypan blue staining.

C. Membrane Isolation—1-8 liter batches of cells at densities of $6-10 \times 10^5$ cells/ml are pelleted in conical bottom glass centrifuge bottles (600 or 800 ml; Bellco) at $1,000 \times$ g for 5 min. The supernatants are carefully poured off and the cells are resuspended in ice cold homogenization medium (1 mM Na-bicarbonate at pH 7.6, 1 mM EDTA and 1 mM EGTA) containing 0.7% (vol/vol) of the "100×4pase" protease inhibitor cocktail (see below). Twenty ml of homogenization medium is used for every liter of suspension culture. After 5 min. on ice, the hypotonically swollen cells are homogenized with 10 strokes of a tight fitting Dounce homogenizer (Kontes, type A pestle). The homogenate is centrifuged at $1,000 \times$ g for 10 min. and the supernatant is removed and kept on ice. The $1,000 \times$ g pellet containing residual intact cells, nuclei and DNA is washed by gently homogenizing with 4 strokes with a type B pestle in one half the original volume of homogenization medium and recentrifuging for 10 min. at $1,000 \times$ g. The final $1,000 \times$ g pellet consists mostly of DNA and is discarded. The $1,000 \times$ g supernatants are combined and centrifuged at $20,000 \times$ g for 30 min. The $20,000 \times$ g pellet is washed twice in 25 mM Tris (pH 7.4), with centrifugation for 25 min. at $20,000 \times$ g. Final membrane pellets are resuspended in 25 mM Tris buffer to concentrations of 4-10 mg membrane protein/ml. Then the $100 \times$ 4pase protease inhibitor cocktails are added to 1% of final volume and aliquots are frozen on dry ice. Membranes are stored at $-90°$ C. until needed. Membrane protein is assayed with the Bradford dye binding assay (Bio-Rad).

D. Protease Inhibitor Mixtures—Three different protease inhibitor mixtures were used for receptor binding assays and receptor purification. A. $40 \times$ PMSF (phenylmethylsulfonyl fluoride)/Baci=2 mg/ml PMSF (Bachem)+2 mg/ml bacitracin (Sigma) dissolved in DMSO. B. $400 \times$ PMSF/Bacitracin=20 mg/ml PMSF and 20 mg/ml bacitracin. Mixtures A and B are used in routine binding assays and in the binding step of the receptor purification protocol. The $40 \times$ concentration is generally used for smaller binding assays where pipetting accuracy of smaller volumes is a factor. Final DMSO concentrations in the binding assays, 0.25-2.5% do not affect ligand binding or any subsequent procedures. C. $100 \times$ 4Pase—7.5 mg/ml leupeptin (Bachem)+14.5 mg/ml PMSF=3 mg/ml chymostatin (Bachem)+1 mg/ml pepstatin A (Sigma) dissolved in DMSO. This mixture is used in membrane solubilization buffers and in all buffers used in receptor purification. All protease inhibitor mixtures are stored as frozen aliquots at $4°-10°$ C. and are added to buffers at appropriate dilutions immediately before use.

E. Receptor Binding Methods

1. Standard Binding Assays—Binding assays are done in a binding buffer containing 50 mM HEPES (pH 7.4), 0.5% BSA and 5 mM $MgCl_2$. The standard assay for [$^{125}$I]SRIF analog binding to $GH_4CL$ membranes, done in 96 well microtiter plates (Dynatech Immulon II Removawell plates), is carried out as follows: 1. Radioligand is diluted in binding buffer+PMSF/Baci to the desired cpm per vol. of 50 $\mu$l and then 50 $\mu$l aliquots are added to the wells. For non-specific binding samples, 5 $\mu$l of 40 $\mu$M cold S14 is also added per well. 2. Binding is initiated by adding 150 $\mu$l per well of membrane diluted to the desired concentration (10-30 ug membrane protein/well) in binding buffer+PMSF/Baci. Plates are then covered with Linbro mylar plate sealers (Flow Labs) and placed on a Dynatech Microshaker II and binding is allowed to proceed at room temperature for 1-2 hours. Binding is stopped by centrifuging the plate for 15 minutes at $2,000 \times$ g. The supernatants are dumped off and membrane pellets washed once by addition of 200 $\mu$l of ice cold binding buffer, brief shaking and recentrifugation. Finally the individual wells are placed in $12 \times 75$ mm tubes and counted in an LKB Gammamaster counter (78% efficiency). Specific binding by this method is identical to that measured when free ligand is removed by rapid (3-5 seconds) filtration and washing on polyethyleneimine-coated glass fiber filters.

Three variations of the standard binding assay are also used.

2. Competitive radioligand binding assays with a concentration range of cold ligand vs. [$^{125}$I]SRIF are carried out as described above with one modification. All dilutions of SRIF analogs being assayed are made in $40 \times$ PMSF/Baci to a concentration $40 \times$ the final concentration in the assay. This gives very consistent results with a wide variety of SRIF structural analogs over a wide range of dilutions. 5 ul samples of peptide are then added per microtiter well. Membranes and radioligand are diluted out in binding buffer without protease inhibitors. Radioligand is added and mixed with cold peptides and then binding is initiated by addition of membranes.

3. Chemical cross-linking of radioligand with receptor is done after a binding step identical to the standard assay. However, the wash step is done with binding buffer minus BSA to reduce the possibility of non-specific cross-linking of radioligand with BSA. The cross-linking step is carried out as described below.

4. Larger scale binding assays to obtain membrane pellets for studies on solubilization of receptor:ligand complex and for receptor purification are also carried out. These are identical to the standard assays except that: (a) Binding is carried out in polypropylene tubes in volumes from 1-250 ml, with the wash step being done in the same volume as initially used for binding, (b) Concentration of membrane protein is always 0.5 mg/ml, (c) For receptor purification, BSA concentration in the binding buffer is reduced to 0.25% and the wash step is done with binding buffer without BSA. This is to reduce BSA contamination of the purified receptor.

F. Chemical Cross-Linking of Radioligand to Receptor—After a radioligand binding step as described above ("Receptor Binding Methods, 3."), the membrane pellets are resuspended in 200 ul per microtiter plate well of ice-cold binding buffer without BSA. Then 5 ul per well of 4 mM N-5-azido-2-nitrobenzoyloxysuccinimide (ANB-NOS, Pierce) in DMSO is added and mixed. The samples are held on ice and UV-irradiated for 10 minutes with a Mineralight R-52G lamp (UVP Inc., San Gabriel, Calif.) at a distance of 5-10 cm. Then the samples are transferred to Eppendorf microfuge tubes, the membranes pelleted by centrifugation, supernatants removed and membranes solubilized in Laemmli SDS sample buffer for polyacrylamide gel electrophoresis (PAGE). PAGE is done as described below and radiolabelled proteins are visualized by autoradiography of the dried gels with Kodak XAR film and Dupont image intensifier screens.

G. Membrane Solubilization—Initial solubilization studies are carried out in buffer containing 25 mM Tris (pH 8), 10% glycerol (wt. vol.) and 0.2 mM $CaCl_2$. Later, $MgCl_2$ is substituted for $CaCl_2$, as mentioned in the text. This will be referred to as "solubilization buffer". The highly soluble detergents including Triton X-100, deoxycholate, deoxycholate:lysolecithin, CHAPS and zwittergent are made up in solubilization buffer at 10% concentrations and stored as frozen aliquots. Lysolecithin is made up fresh because of insolubility upon freeze-thawing and digitonin is made fresh at lower concentrations due to its more limited solubility.

To solubilize membranes, washed pellets after the binding step are resuspended free of visible particles by pipetting and vortexing in solubilization buffer+1/100 (vol/vol) of 100× 4Pase protease inhibitors+detergent at the desired concentration. After 1 hour on ice, the samples are centrifuged at 100,000×g for 30 minutes. The supernatants are removed and held on ice and the pellets are discarded.

H. Assay of Solubilized Receptors—After binding of [$^{125}$I]SRIF analogs and solubilization of the membranes with detergent, the intact R:L complex could be assayed by four different methods (all carried out on ice or in a cold room at 4°-10° C.): (1) Column chromatography (Knuhtsen et al., Biochem. J. 254:641-647, 1988). Sephadex G-50 columns (8×130 mm) are equilibrated with solubilization buffer containing detergent at the concentration used to solubilize membranes and 1 mg/ml bovine serum albumin. 0.2-0.5 ml samples of solubilized membranes are applied to the columns and eluted at a flow rate of about 0.7 ml/minute. 0.18 ml samples are collected. Radioactivity is determined in a gamma counter as described under "Receptor Binding Methods". Void volumes of the columns are determined by the elution volume of blue dextran. Radioactivity eluting in the void volume (>50,000 MW) was considered bound to protein. Radioactivity eluting later, at the same volume as free [$^{125}$I]SRIF, is considered non-bound. (2) Polyethyleneglycol precipitation (Cuatrecasas, PNAS USA 69:318-322, 1972) For 1 part (100-250 ml) of solubilized membranes in a 12×75 mm polypropylene tube, 5 part (0.5-1.25 ml) of 1% (w/v) bovine gamma globulin (Sigma) in 0.1M sodium phosphate buffer is added, followed by 5 parts (0.5-1.25 ml) of 25% (w/v) polyethyleneglycol (Sigma) and mixing. The mixture is held on ice for 15 minutes. Then 3 ml of 0.1M sodium phosphate (pH 7.4) is added to a final part of 4 ml per sample and the samples are rapidly (1-3 seconds) filtered over Whatman GF/B glass fiber filters and washed with 4 ml of the phosphate buffer. PEG precipitated SRIF receptor: [$^{125}$I]SRIF complex is determined by gamma counting of the filters. (3) GFB/PEI filter binding (Bruns et al., Analytical Biochem. 132:74-81, 1983). Whatman GF/B glass fiber filters are soaked in 0.3% polyethyleneimine (PEI, Sigma) for 3 hours. 25-100 ul samples of solubilized membranes are placed in 12×75 mm polypropylene tubes. Then 4 ml of solubilization buffer (without detergent) is added per sample and the samples are immediately filtered through the GFB/PEI filters (1-3 seconds) and washed with 4 ml of solubilization buffer. CPM of SRIF receptor: [$^{125}$I]SRIF complex adsorbed to filters are determined by gamma counting. (4) Charcoal/Dextran (Paul and Said, Peptides 7[Suppl. 1]: 147-149, 1986). 0.5 gm of Dextran T70 (Pharmacia) is dissolved in 1 liter of water and then 5 gm of activated charcoal (Norit A, alkaline; Fisher Scientific) is added. The suspension is stirred for 10 minutes at room temperature and then stored at 4° C. until use. To measure R:L complex, 4 parts by volume of charcoal/dextran suspension are added to 1 part by volume of solubilized membrane. The samples are mixed and held on ice for 2 minutes and then centrifuged for 2 minutes at 11,000×g in a Beckman microfuge. Free radioligand is adsorbed to charcoal/dextran and is discarded with the pellet. SRIF receptor: [$^{125}$I]SRIF complex remains in the supernatant and is determined by gamma counting.

I. Receptor Purification

1. Binding of biotinyl-SRIF to $GH_4Cl$ membranes. The binding step is carried out as described in Section 4 of "Receptor Binding Methods". Incubations are for 1 hour at room temperature. In the standard purification protocol, the binding incubations contain 10 nM Bio-S29/[$^{125}$I]Bio-S28 is added as a tracer at levels of 5,000-100,000 cpm per mg of membrane protein. Control incubations contain 10 uM cold S14 to saturate the receptor with non-biotinylated ligand.

2. Solubilization of receptor:ligand complex. This is done as described ("Membrane Solubilization"), with 0.15% deoxycholate:lysolecithin in solubilization buffer containing 0.2 mM $MgCl_2$, to obtain 100,000×g supernatants containing solubilized R:L complex.

3. Adsorption of solubilized R:L complex to streptavidin. Immobilized streptavidin (streptavidin crosslinked to 6% beaded agarose, Pierce Chemical Co.; "SA-agarose") is washed in solubilization buffer and added to the solubilized membranes as 1/30 of the final volume. This mixture is incubated with constant stirring by end-over-end rotation for 4-5 hours at 4°-10° C. Then the mixture is applied to a column and the non-bound material is washed through. Binding of radioligand to SA-agarose is determined by comparing cpm in the 100,000×g supernatant with that in the column effluent after adsorption to SA-agarose. Finally, the column is washed with 12-15 column volumes of solubilization buffer+0.15% deoxycholate:lysolecithin+1/500 (vol/vol) 100×4pase.

4. Elution of streptavidin column. The column is eluted with solubilization buffer+0.1 mM EDTA+0.1 mM EGTA+0.1 mM GTP-gamma-S (Sigma)+0.15% (wt/vol) deoxycholate:lysolecithin+1/1000 (vol/vol) 100×4pase. First, one column volume of elution buffer is passed through the column and flow is stopped for 20-30 minutes. Then 3-4 more column volumes of elution buffer are passed through. All the eluates are pooled.

5. Wheat germ agglutinin purification of receptor-Eluates from the streptavidin column are incubated overnight at 4°-10° C. (12-15 hours) with immobilized wheat germ agglutinin (WGA agarose, Vector Labs) to adsorb the SRIF receptor via interaction of covalently bound carbohydrate with the WGA lectin. The ratio (vol/vol) of WGA-agarose to streptavidin column eluate is generally 1:400. A range from 1:1000 to 1:200 gives very similar results. After the binding step, the resin is pelleted by centrifugation, the supernatant is removed and saved, and the resin is washed 3 times (about 2 minutes each) in buffer containing 50 mM HEPES (pH 8), 5 mM $MgCl_2$ and 0.15% deoxycholate:-lysolecithin. To elute the WGA-bound receptor, the resin is extracted three times by repeated mixing (vortex mixer on low speed) over a 15-30 minute period on ice, with 3 resin columns each time, of 10 mM N-N'-N''-triacetylchitotriose in the same HEPES buffer (vide supra) used to wash the resin. After each elution step, the resin is centrifuged down and the supernatant is carefully removed, free of WGA-agarose pellets. The three, pooled eluates contain the final, purified SRIF receptor. The material non-bound to WGA contains G protein subunits specifically eluted from the streptavidin column plus non-specific contaminants. All these fractions are stored frozen at $-90°$ C.

J. Miscellaneous Preparative and Analytical Methods

1. SDS-polyacrylamide gel electrophoresis. Electrophoretic separation of proteins, solubilized in 1% SDS (in Laemmli sample buffer)+5 mM dithiothreitol for 5-10 minutes at 90° C., is done in 12% SDS-polyacrylamide gels by the method of Laemmli (Nature 227: 680-685, 1970). Stacking gels are composed of 3.8% polyacrylamide. For regular silver staining of proteins bands the gels are fixed in 40% methanol+10% acetic acid and then stained with the Bio-Rad silver staining kit (Bio-Rad Labs). For silver staining of glycoproteins, the gels are stained by the method of Jay et al. (Analytical Biochem. 185: 324-330, 1990), with prestaining by the dye alcian blue. This method is necessary for silver staining of heavily glycosylated proteins such as the SRIF receptor.

2. Concentration and extraction of protein samples for analysis. Prior to gel electrophoresis, amino acid analysis and sequencing, samples are concentrated in Centricon-30 microconcentrators (Amicon Co.). One to two ml samples are placed in the microconcentrator tubes and centrifuged at $3,000 \times g$ to pass excess buffer through the filters. Samples are concentrated to volumes of 50-150 ul and transferred to 1.5 ml, Eppendorf microfuge tubes. Then the samples are extracted in $CHCl_3$: $MeOH$:$H_2O$ to remove detergents and buffer and obtain a dry protein pellet (Wessel and Flugge, Analytical Biochem. 138: 141-143, 1984). This pellet could be solubilized in SDS sample buffer for PAGE or in other solvents such as 70% formic acid or 8M urea for other purposes such as generation of proteolytic peptides, amino acid analysis and sequencing.

3. Preparation of radioligands for receptor binding assays. SRIF analogs are radioiodinated by the chloramine-T method. The reagents are added to 1.5 ml siliconized Eppendorf centrifuge tubes as follows: (a) 5 ul of peptide (0.5 mg/ml) in 50 mM potassium phosphate buffer (pH 7.4), (b) 5 ul of 100 mM potassium phosphate buffer (pH 7.4), (c) 5 ul of methanol, (d) 4 ul of Na[$^{125}$I] (Amersham, 100 uDi/ml; cat.=IMS.30), mix by vortexing, add reagent (e) 5 ul of 0.7 mM chloramine-T (Kodak), mix by vortexing and allow 20 seconds reaction time, add (f) 5 ul of 2 mM tyrosine in 0.1% TFA. Immediately after reaction, the samples are injected onto a Supelco LC-308 column (c-8 reverse phase, 5 u particle size, 300 angstrom pore size, column dimensions=$0.46 \times 5$ cm). Labelled peptides are eluted isocratically at 20-26% acetonitrile (depending on the peptide) in water/0.1% TFA. Monoiodinated SRIF analogs are very efficiently separated from noniodinated peptide by this method. We have established this by kinetic studies with nonradioactive iodide and correlation with radiolabelling patterns. Therefore, the monoiodinated analogs are considered to have specific radioactivities of 2,200 Ci/mmole, the same as [$^{125}$I]. 0.1 ml radioactive peptide fractions off the column are collected into 0.1 ml volumes of 2% BSA in 1% acetic acid. The most active fractions are pooled, aliquoted and stored frozen at $-20°$ C.

II. SOLUBILIZATION OF PREBOUND LIGANDS

Certain types of receptors, such as the somatostatin receptor exemplified here, are extremely difficult to solubilize in active form from cell membranes. Initial experiments are therefore conducted to determine the feasibility of solubilizing instead a receptor:radioligand complex after binding of radioligand to the membrane-bound receptor. The method employed is that disclosed in Knuhtsen et al. (Biochem. J. 254: 641-647, 1988; also described in detail in "Methods: Membrane Solubilization") with solubilization in 1% CHAPS.

[$^{125}$I]Tyr11-S14 is bound to $GH_4C_1$ membranes as described above ("Methods: Receptor Binding Methods, 4."), except that these binding assays contain 2 mg membrane protein in 8 ml (0.25 mg membrane protein/ml). Radioligand is $6 \times 10^{-6}$ cpm/8 ml. A nonspecific binding sample is identical except for the addition of 1 uM cold S14. Initial cpm bound is $1.43 \times 10^6$ (total) and $0.65 \times 10^6$ (nonspecific). After the binding step, membranes are solubilized in solubilization buffer containing 0.2 mM $CaCl_2$ and 1% CHAPS ("Methods: Membrane Solubilization"). CPM in the $100,000 \times g$ supernatants are $0.61 \times 10^6$ (total) and $0.29 \times 10^6$ (nonspecific). Free [$^{125}$I]Tyr11-S14 is added to the nonspecific binding sample to give equal cpm in the two samples. Then 0.25 ml aliquots of each supernatant (75-80,000 cpm) are loaded onto $0.8 \times 13$ cm columns of Sephadex G-50. The columns are eluted as described in "Methods: Assay of Solubilized Receptors, 1." and the fractions counted for radioactivity.

FIG. 1 shows the profile of CHAPS solubilized R:L complex on a Sephadex G-50 column. A peak of high MW material eluting in the column void volume (peak I; 34% of total cpm) contain specifically bound radioactivity. This is shown by greatly reduced recovery of radioactivity in peak I from a nonspecific binding sample, where the binding assay is done in the presence of excess non-radioactive S14 ("+ excess cold S14" sample, FIG. 1). Peak II in FIG. 1 represents free [$^{125}$I]-Tyr11-S14, and is the major peak in the nonspecific binding sample. In FIG. 1 it is important to note that just before applying samples to the columns, free [$^{125}$I]-Tyr11-S14 is added to the non-specific binding sample to equalize the cpm in the two samples. Specifically bound ligand, calculated from the difference in peak I cpm between the two samples is 11% of the initial specifically bound cpm on the intact membranes, indicating that receptor:ligand complex is recovered, albeit at relatively low levels. In this same experiment, two alternate separation methods, polyethylene glycol precipitation and adsorption of complex to polyethyleneimine (PEI) coated Whatman GFB glass fiber filters (both methods described in "Methods: Assay of Solubilized Receptors, 2 and 3") are employed and slightly improved results are obtained with the GFB/PEI filters (Table 1). The GFB/PEI method is used in subsequent experiments.

TABLE 1

Recovery of Solubilized Somatostatin Receptor:[$^{125}$I]Tyr11-S14 Complex by Three Different Methods 0.25 ml samples containing solubilized R:L complex, from the preparation described in FIG. 1 are separated from free radioligand either by: (1) chromatography on Sephadex G-50 (see FIG. 1), (2) Precipitation with polyethyleneglycol+bovine gamma globulin with collection of the precipitates on GFB filters or (3) adsorption on polyethyleneimine-coated, GFB filters (for methods 2 and 3 see "Methods: Assay of Solubilized Receptors, 2 and 3"). Radioactivity recovered in peak I (Method 1) or on filters (Methods 2 and 3) is compared in the Table.

| Method | CPM of [$^{125}$I]Tyr11-S14 Recovered | | Specifically Bound Ligand Recovered (A-B) |
|---|---|---|---|
| | A. Total[1] | B. Nonspecific[2] | |
| 1. Sephadex G-50 | 23,944 | 9,104 | 16,840 |
| 2. PEG precipitation | 23,075* | 7,803* | 17,272 |
| 3. GFB/PEI filters | 27,533* | 7,193* | 20,340 |

[1] = Initial binding done in absence of $10^{-6}$ M cold S14.
[2] = Initial binding done in presence of $10^{-6}$ M cold S14.
* = Triplicate determinations. SE 5%.

Detergent Selection for Solubilization

In an attempt to improve the recovery of receptor:ligand complex after solubilization, experiments are conducted to evaluate the ability of various types of detergents to both solubilize substantial quantities of the complex, and to maintain the integrity of the complex after solubilization. Binding incubations with GH$_4$C$_1$ membranes and [$^{125}$I]Tyr11-S14 ("Methods: Receptor Binding Methods, 4.": 0.5 mg membrane protein/ml in all assays; 200,000-500,000 cpm[$^{125}$I]Tyr11-S14/ml") are followed by detergent solubilization of membranes ("Methods: Membrane Solubilization"). CPM of radioligand in the supernatants are determined by gamma counting and solubilization of specifically bound radioligand is calculated by comparison with non-solubilized membranes.

Figure 2:
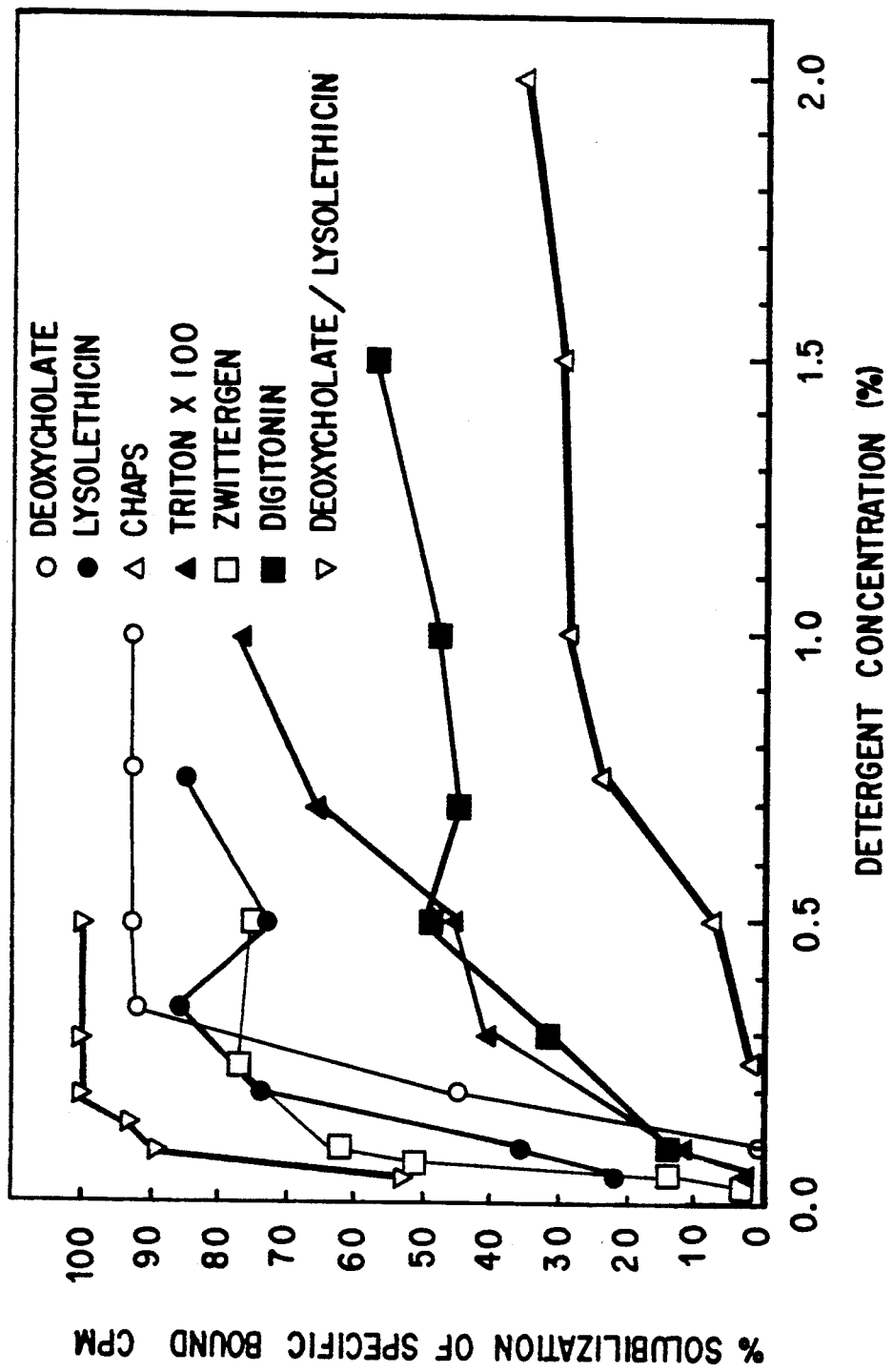
FIG. 2 illustrates the comparative solubilization of specific bound radioligand from cell membranes utilizing a variety of different detergent types.
Figure 3:
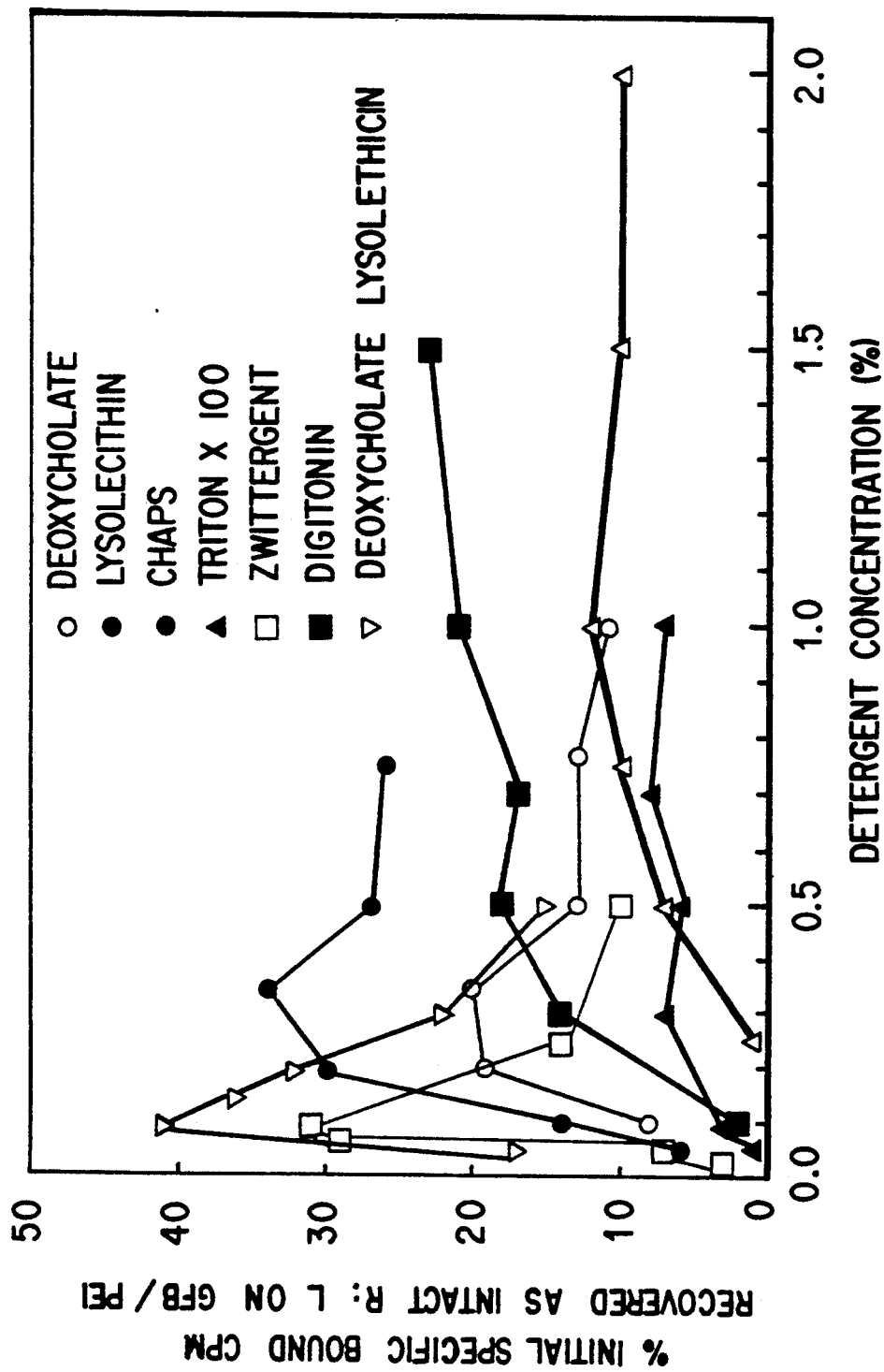
FIG. 3 illustrates the comparative recovery of intact receptor:ligand complex from 100,000 g supernatants for various detergents at different concentrations.

FIG. 2 shows the results of this study. Data is expressed as % solubilization of cpm specifically bound to membranes. The graph shows that deoxycholate, both alone and in combination with lysolecithin, provides superior solubilization of receptor:ligand complex, with zwittergent, lysolecithin, digitonin and Triton X-100 providing less satisfactory but adequate levels of solubilization. CHAPS, on the other hand, did not solubilize well at all at any concentration tested.

The detergents are then tested for their ability to maintain the stability of the receptor:ligand complex. The supernatants from the previous experiment are run over polyethylenemine-coated glass fiber filters, and the amount of specific bound radioligand recovered on the filters is determined. The percentage of initial specific bound radioligand recovered as intact complex is then determined. These results are presented in FIG. 3. In this case, superior stabilizing properties are seen with deoxycholate/lysolecithin, zwittergent, and CHAPS.

In a third set of trials, procedures as noted above are performed using the biotinylated ligand, biotinyl-NH(Leu8, D-Trp22, [$^{125}$I]Tyr25)SRIF (hereinafter [$^{125}$I]BioS28) for receptor binding. The detergents employed are the same, using the predetermined optimal concentrations of each, with the exception of Triton X-100, which is already eliminated as a potential choice because of its poor capacity to stabilize the receptor:ligand complex. Membrane solubilization is conducted as already described; however, determination of the presence of the intact receptor:ligand complex in the 100,000×g supernatant is accomplished by charcoal/dextran assay ("Methods: Assay of Solubilized, 4."). The results of this assay are presented in Table 2A. As in the previous experiments, the deoxycholate:lysolecithin combination provides superior solubilization and stabilization of the receptor:ligand complex with satisfactory results also being shown by deoxycholate, lysolecithin and digitonin.

The final determination is whether the detergent interferes with binding of the receptor:[$^{125}$I]BioS-28. The 100,000×g supernatants are mixed with 1/20 volumes of streptavidin-agarose, (hereinafter referred to as "SA") for 4 hours at 4°-10° C. R:L complex in the supernatants ("non-bound to SA") after this time is measured by the charcoal/dextran assay. The % of non-bound, intact R:L complex is calculated from the ratio (R:L non-bound to SA/original R:L in the 100,000×g supernatant). The % of intact R:L complex bound to SA is calculated by subtracting % non-bound R:L from 100%. Finally, % of original R:L bound to SA = % R:L bound to SA × % solubilization of original membrane-bound R:L complex. As can be seen by reference to Table 2B, deoxycholate, digitonin and combined deoxycholate:lysolecithin show the least interference with binding ability. As the final column in Table 2B shows, overall, the deoxycholate:lysolecithin combination is most efficient in the procedure as a whole in recovering receptor, with satisfactory results also being observed with deoxycholate and digitonin.

TABLE 2A

Solubilization of Receptor:Ligand Complex

| Detergent | Solubilization of Specifically Bound CPM (%)* | Solubilized CPM in Intact R:L Complex (%)# | % Solubilization of Original R:L in Membranes (A × B) |
|---|---|---|---|
| CHAPS | 38 | 32 | 12 |
| Digitonin | 55 | 50 | 28 |
| Deoxycholate | 93 | 33 | 31 |
| Lysolecithin | 73 | 46 | 33 |
| Zwittergent | 72 | 34 | 24 |
| Deoxycholate: Lysolecithin | 76 | 53 | 41 |

Notes:
*Based on 14,013 cpm of specifically bound [$^{125}$I]Bio-S28 per sample and recovery of cpm in 100,000 × g supernatant
R:L complex in 100,000 × g supernatant assayed by charcoal/dextran method

TABLE 2B

Binding of Solubilized R:L Complex to Streptavidin

| Detergent | % of Intact R:L Nonbound to SA in 5 Hours | % of Intact R:L Bound to SA (100% - A) | % of Original R:L Complex Bound to SA* |
|---|---|---|---|
| CHAPS | 44 | 56 | 7 |
| Digitonin | 13 | 87 | 24 |
| Deoxycholate | 11 | 89 | 29 |
| Lysolecithin | 65 | 36 | 16 |
| Zwittergent | 51 | 49 | 17 |
| Deoxycholate: Lysolecithin | 14 | 86 | 34 |

Note:
*% R:L bound to SA × % solubilization of original R:L complex

III. PURIFICATION OF THE SRIF PITUITARY RECEPTOR

Receptor-Binding Characteristics of Biotinyl-SRIF Analogs

Four biotinylated SRIF analogs are synthesized ("Methods: Synthesis of Peptides"). Their structures and abbreviated designations are as follows:
Biotinyl-NH—SRIF14=Bio-S14
Biotinyl-[NH—(CH$_2$)$_5$—CO]—NH-(Tyr11)-SRIF14=Bio-6C-S14
Biotinyl-[NH—(CH$_2$)$_5$—CO]$_2$—NH-(Tyr11)-SRIF14=Bio-12C-S14
Biotinyl-NH-(Leu8, D-Trp22, Tyr25)SRIF28=Bio-S28

Figure 4A:
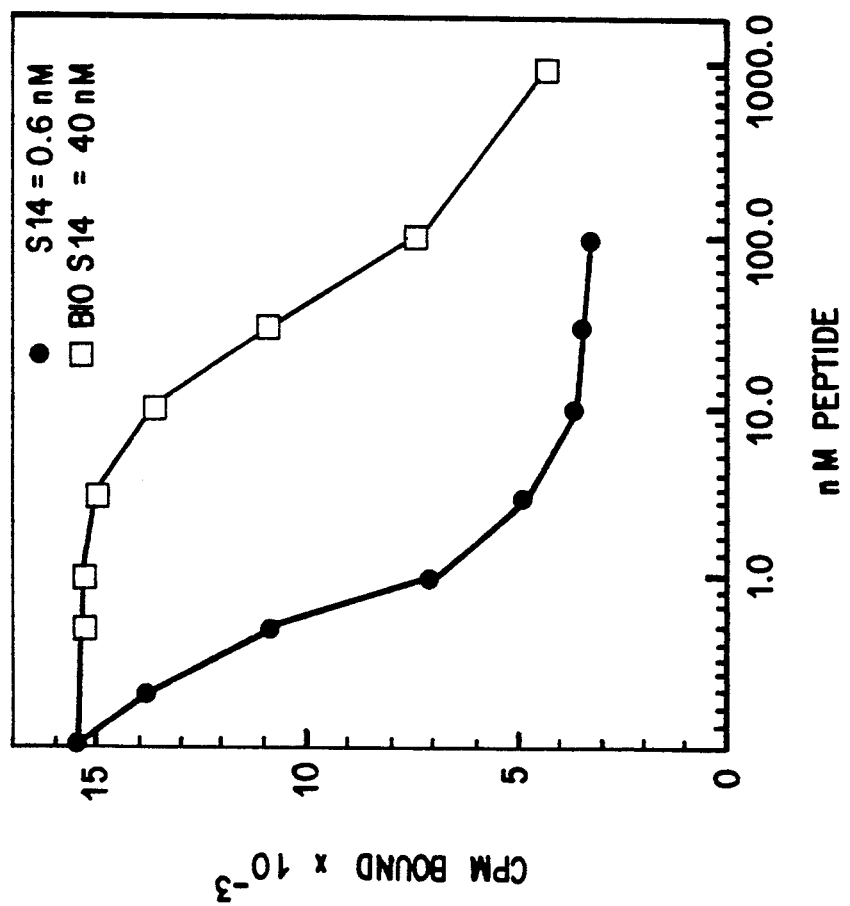
FIG. 4 illustrates the relative potencies of various synthetic biotinylated SRIF ligands in a competitive binding assay with non-biotinylated ligands. (A) shows a comparison with biotinylated ligand with no spacer; (B) shows a comparison of biotinylated ligands with spacers.

FIG. 4 shows the potencies of these peptides relative to each other and to S14 in competitive binding assays with [$^{125}$I]Tyr11-S14 and GH$_4$C$_1$ membranes. These assays are carried out as described in Methods: Receptor Binding Methods, 2". The first SRIF analog synthesized, Biotinyl-NH-S14, contains no spacer between the biotinyl and S14 moieties and has only about 1.5% the potency of S14 in the competitive binding assay (FIG. 4A; assays contained to 40 ug of GH$_4$C$_1$ membrane protein and 85,000 cpm of radioligand). Therefore the Bio-6C-S14, Bio-12C-S14 and Bio-S28 analogs are preferably synthesized. In Bio-S28, amino acid residues 1-14 are considered a spacer since residues 15-28 are equivalent to an S14 analog, having all the necessary structure for high affinity binding. The three spacer-containing biotinyl SRIFs show receptor binding activity similar to that of S14 (FIG. 4B; assays contain 20 ug of GH$_4$C$_1$ membrane protein and 100,000 cpm of radioligand). The IC$_{50}$s and relative potencies are S14 (0.2 nM)>Bio-S28 (0.3 nM)>Bio-6C-S14 (2 nM)>Bio-12C-S14 (2 nM).

Figure 5:
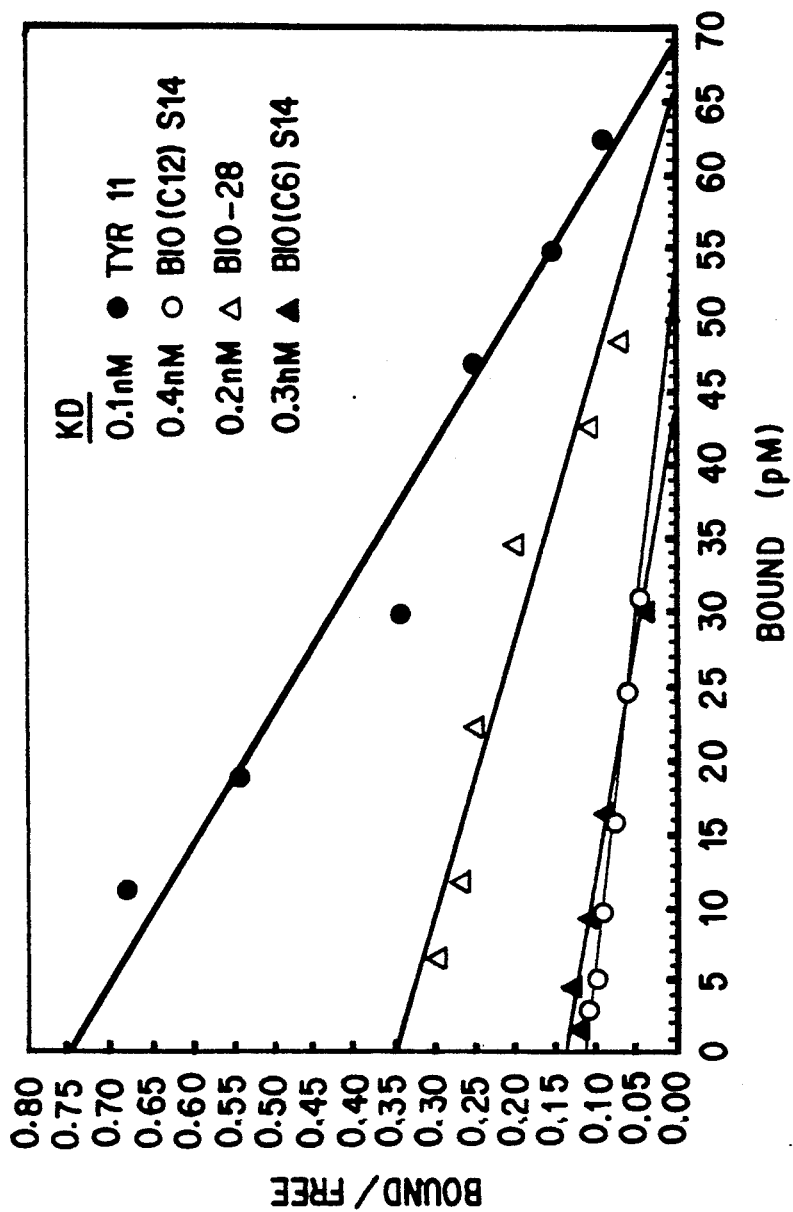
FIG. 5 illustrates a comparison of the relative binding affinities of three biotinylated ligands compared with a non-biotinylated ([$^{125}$I]Tyr11-S14) ligand.

Because Bio-6C-S14, Bio-12C-S14 and Bio-S28 all contain tyrosine residues, it is possible to prepare their [$^{125}$I] labelled analogs and carry out Scatchard analyses of their binding affinities relative to [$^{125}$I]Tyr11-S14 (FIG. 5). As shown in the figure, the [$^{125}$I]-labelled peptides fall in the same order of potency as their non-labelled forms. The dissociation constants ($K_D$) and relative binding affinities are [$^{125}$I]Tyr11-S14 (0.1 nM)>[$^{125}$I]Bio-S28 (0.2 nM)>[$^{125}$I]Bio-6C-S14 (0.3 nM)>[$^{125}$I]Bio-12C-S14 (0.4 nM).

Streptavidin Binding Characteristics of Biotinyl-SRIF Analogs

The three, high-affinity binding, biotinyl-SRIF analogs (Bio-6C-S14, Bio-12C-S14 and Bio-S28) all appear to be useful for SRIF receptor purification. However, Bio-S28 is selected for further use in SRIF receptor purification because it binds to the SRIF receptor with the highest affinity (FIGS. 4 and 5) and because the solubilized R:L complex made with [$^{125}$I]Bio-S28 binds somewhat better to immobilized streptavidin than the R:L complexes with Bio-6C-S14 and Bio-12C-S14 (see Table 2).

To compare the three biotinyl-SRIF analogs in terms of binding to streptavidin, the following experiment is done. [$^{125}$I]Bio-SRIF analogs are bound to GH$_4$C$_1$ membranes as described ("Methods: Receptor Binding Methods, 4"). All radioligands are at a concentration of 0.77×10$^6$ cpm/ml. For each radioligand, a control for non-specific binding is done in the presence of 1 uM cold S14. CPM bound/mg membrane protein after the binding step are as follows: [$^{125}$I]Bio-6C-S14=755,020 (total) and 43,361 (non-specific); [$^{125}$I]Bio-12C=S14=633,134 (total) and 39,538 (nonspecific); [$^{125}$I]Bio-S28=1,065,512 (total) and 35,049 (nonspecific). The membrane pellets are solubilized in solubilization buffer containing 0.15% deoxycholate:lysolecithin and 0.2 mM MgCl$_2$ as described ("Methods: Membrane Solubilization"). It should be noted that Mg$^{2+}$ can replace Ca$^{2+}$ in the solubilization buffer, giving equally effective recovery of intact R:L complex and reducing the possibility of Ca$^{2+}$-dependent proteolysis. One ml samples of solubilized membranes are incubated with 0.05 ml vols of streptavidin-agarose at 4°-10° C. on a tube rotator for the times shown. Non-specific binding samples are not done due to the low levels of non-specific binding. At the times shown, the SA beads are spun down and 100 ul samples of supernatant are counted. The cpm are compared to initial cpm in the sample and % binding to SA is calculated from this. The results are presented in Table 3. Also, it should be noted that binding of cpm from the supernatant is considered to parallel the binding of R:L complex. Several observations confirm that this is a valid assumption.

Table 3

Binding of [$^{125}$I]-Labelled Biotinyl-SRIFs to Immobilized Streptavidin

CPM are determined for 100 ul samples of initial 100,000×g supernatant (containing soluble R:L complex) and supernatant after incubation with SA-agarose for times shown.

| | | % Binding of Radioligand to SA-Agarose = (CPM Non-bound/Initial CPM) | | | |
|---|---|---|---|---|---|
| | | 1 hour | | 3 hours | |
| Radioligand | Initial CPM | CPM | % Bound* | CPM | % Bound |
| [$^{125}$I]Bio-6C-S14 | 63,490 | 28,381 | 55% | 16,228 | 74% |
| [$^{125}$I]Bio-12C-S14 | 54,344 | 23,391 | 57% | 13,071 | 76% |
| [$^{125}$I]Bio-S28 | 92,534 | 31,645 | 66% | 17,098 | 82% |

*Calculated as ... 100% - [(Non-bound CPM/Initial CPM) × 100%]

Purification of SRIF Receptor

A preparation of SRIF receptor is purified from 17 mg GH$_4$C$_1$ pituitary cell membranes as described in "Methods: Receptor Purification". Some important features of this experiment are as follows: Two 17 mg samples of membranes are used. Both are incubated with 10$^{-8}$M Bio-S28. However, one sample also receives 10$^{-5}$M non-biotinyl S14 for 23 minutes before addition of any Bio-S28. This serves to block binding of Bio-S28 and creates a control to show non-specific binding of proteins to the streptavidin column. Also, each sample received 1.5×10$^8$ cpm of [$^{125}$I]Bio-S28 as a tracer. This is added 2-3 minutes before the addition of cold Bio-S28. After a 1-hour binding step, the membranes are washed in binding buffer without BSA and solubilized in solubilization buffer containing 0.15% deoxycholate:lysolecithin and 0.2 mM MgCl2. Each 100,000×g supernatant (17 ml) is incubated with 0.6 ml of streptavidin-agarose for 4 hours at 4°-10° C. The SA-agarose is transferred to a 0.7 cm diameter column, washed and eluted with EDTA/EGTA/GTP-gamma-S as described ("Methods: Receptor Purification").

Radioligand is followed through the procedure to estimate solubilization of R:L complex and % initial binding of R:L complex to immobilized streptavidin. This is shown in Table 4 below.

TABLE 4

Use of [$^{125}$I]Bio-S28 to Trace SRIF R:L Complex During Purification on Immobilized Streptavidin

| Ligand in Binding Step | CPM Initially Bound to Membranes | CPM Solubilized by Deoxycholate: Lysolecithin | Solubilized CPM Non-Bound to Streptavidin |
|---|---|---|---|
| $10^{-8}$ M Bio-S28 | 59,132 | 54,094 (91%) | 14,960 (28%) |
| $10^{-8}$ M Bio-S28 + $10^{-5}$ M S14 (NSB) | 9,316 | 6,834 (73%) | 1,054 (15%) |

A calculation from Table 4 shows that 72% of the specifically bound radioligand is bound to streptavidin. As discussed above, this should approximate the binding of R:L complex to streptavidin.

EDTA/EGTA/GTP-gamma-S is used to elute SRIF receptor from streptavidin columns because the soluble R:L complex is dissociated by this combination of agents. For the SRIF R:L complex solubilized in 0.15% deoxycholate:lysolecithin, 0.1 mM EDTA+0.1 mM EGTA+0.1 mM GTP-gamma-S gives 75-90% dissociation. This is probably due to initial dissociation of G-protein from the receptor and consequent lowering of ligand binding affinity.

Figure 6:
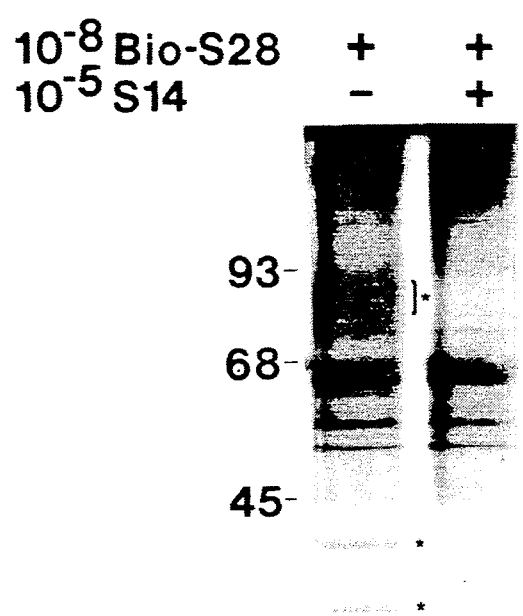
FIG. 6 illustrates the EDTA/EGTA/GTP-gamma-S eluate from a streptavidin column run on 12% SDS-PAGE. The diffuse band with molecular weight of between 75–95,000 daltons represents the SRIF receptor glycoprotein, while the two narrowly focused bands, molecular weights of 40,000 and 35,000, are the associated G protein subunits.

The EDTA/EGTA/GTP-gamma-S eluates from streptavidin are concentrated by Centricon-30 filters and solvent extraction and then solubilized in SDS and separated on 12% SDS-polyacrylamide gels ("Methods: Miscellaneous preparative and Analytical Methods, 1, 2"). Staining of the gels by alcian blue/silver ("Methods: ibid") reveals three protein bands that are specifically bound to and eluted from streptavidin (FIG. 6). One is a diffuse, 75-95,000 MW band. The two other specific bands are more sharply focused and have MWs of about 40,000 and 35,000. There are several non-specific bands that also appear in the sample where specific binding of Bio-S28 is blocked by a 1000-fold excess of non-biotinylated S14 ("+$10^{-5}$ S14" in FIG. 6).

Figure 7:
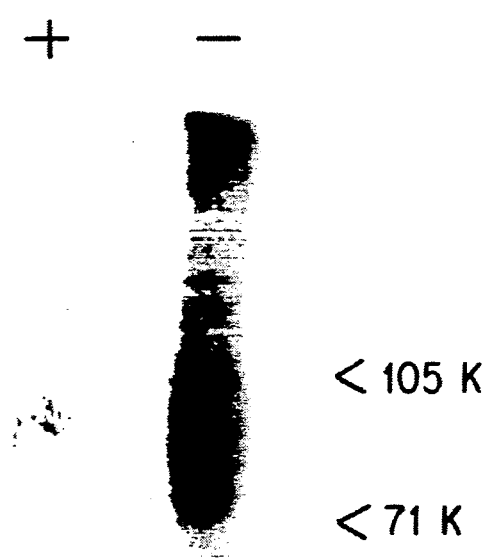
FIG. 7 illustrates the same molecular weight product, presumably the SRIF receptor, as obtained by chemical cross-linking of the receptor to the ligand in the presence (+) or absence (−) of 1 uM cold S14 to block specific binding. The receptor:ligand complex only occurs if receptor sites are not blocked by cold S14.

The diffuse, 75-95K band appears to be the SRIF receptor. It is specific for Bio-S28 (FIG. 6) and has the same size as the SRIF receptor as shown by chemical cross-linking of receptor and radioligand followed by SDS-PAGE separation and autoradiography (FIG. 7). For FIG. 7, cross-linking and autoradiography is done as described in ("Methods: Chemical Cross-linking of Radioligand to Receptor"). The receptor also appears to be a glycoprotein. Thus, it is poorly stained by regular silver staining methods but is well stained by silver if oxidized by periodate and prestained with alcian blue (Jay et al., analytical Biochem. 185:324-330, 1990).

Figure 8:
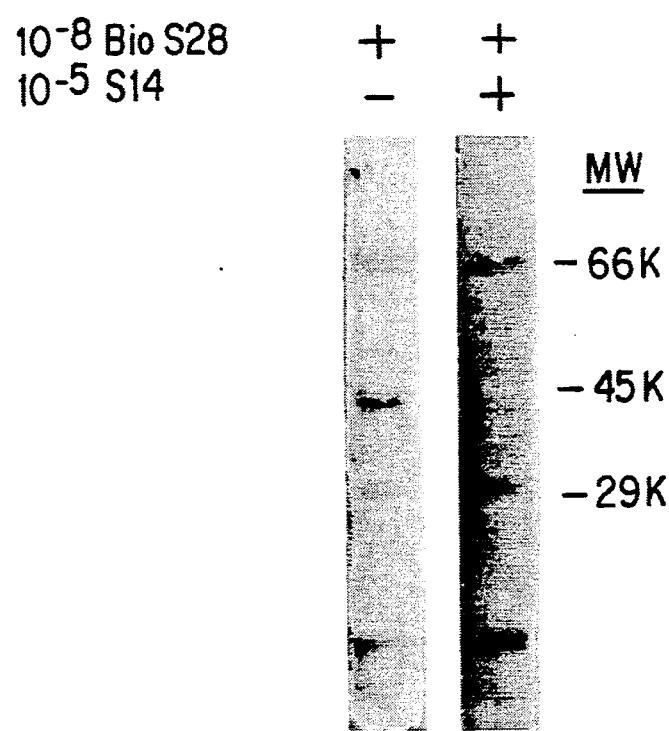
FIG. 8 illustrates the results of an experiment in which samples equivalent to those shown in FIG. 6 are reacted with pertussis toxin and [$^{32}$P]NADH (see text); [$^{32}$P] labelled proteins are separated on 12% SDS-PAGE and visualized by autoradiography. A protein of about 40K is only seen in the sample with Bio-S28 specifically bound ("$-10^{-5}$ S14) prior to purification of receptor on SA-A, confirming the identity is a G protein.

The 40K and 35K proteins have appropriate sizes for G protein alpha and beta subunits respectively. The 40K protein is functionally identified as a G-alpha subunit by the technique of ADP-ribosylation (FIG. 8). Here, pertussis toxin catalyzes transfer of [$^{23}$P]ADP-ribose from NADH to protein. This reaction is shown to be highly specific for G-alpha subunits of the "i" and "o" subtypes (Stadel and Lefkowitz, ibid). In FIG. 8, [$^{32}$P] labelling of a 40K protein in the presence of pertussis toxin and [$^{32}$P]NADH occurs in the streptavidin eluates with samples initially incubated with $10^{-8}$M Bio-S28 but not if Bio-S28 binding is blocked by excess non-biotinylated S14.

Figure 9:
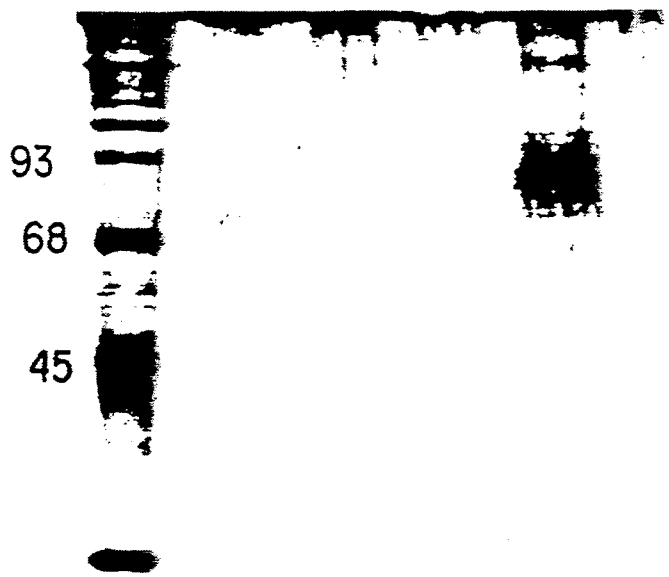
FIG. 9 illustrates the contents of the EDTA/EGTA/GTP-gamma-S eluate after application to WGA agarose and elution with 10 mM sugar. A diffuse band showing the expected molecular weight glycoprotein is clearly shown when the WGA eluate is run on 12% SDS-PAGE.

Finally, when the EDTA/EGTA/GTP-gamma-S eluate from streptavidin is incubated with immobilized wheat germ agglutinin (WGA-agarose), the 75-95K SRIF receptor binds and can be eluted in nearly pure form by 10 mM N-N'-N"-triacetylchitotriose (FIG. 9; WGA binding and elution done as in "Methods: Receptor Purification. 5"; SDS-PAGE and alcian blue/silver staining done as previously described). FIG. 9 shows 1% of a purified sample obtained from 750 mg of $CH_4C_1$ membrane protein. SRIF receptor of this purity is consistently obtained by the methods described herein.

IV. PURIFICATION METHOD AS RECEPTOR ASSAY

Figure 10A:
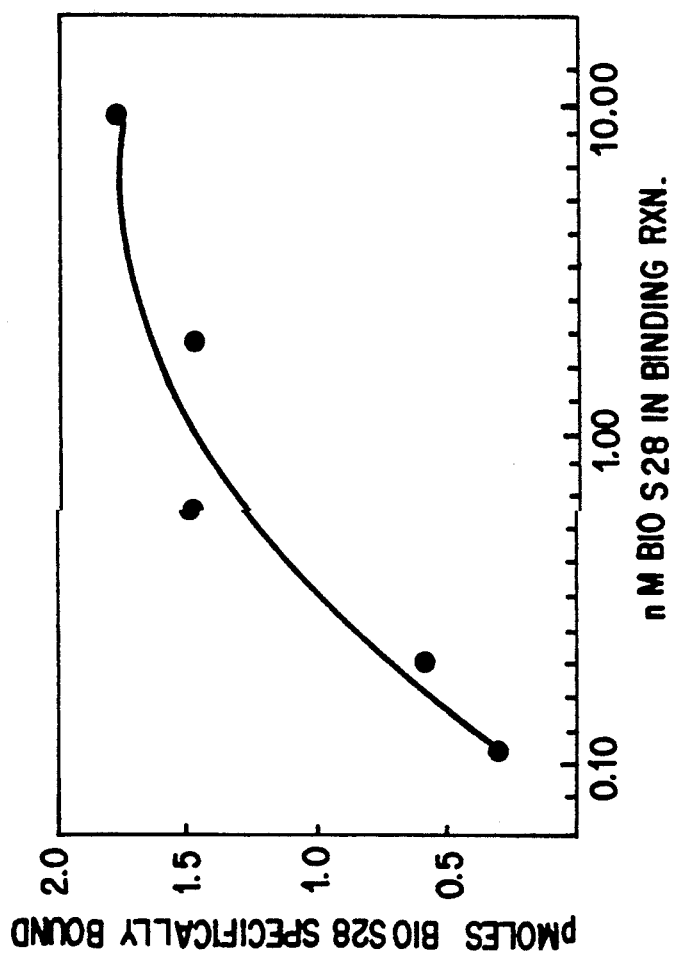
FIG. 10 illustrates the use of the purification method as a quantitative assay for receptor. (A) shows that increasing amounts of BioS28 bind to membranes until saturation is nearly reached, in the presence of 10 nM B28 at the binding step. (B.1) shows SDS-PAGE of each of the points on the binding assay after solubilization, binding and elution from SA-A, and binding and elution from WGA agarose. (B.2) shows the SDS-PAGE of non-bound material from the (B.1) procedure.

The present method can also be used simultaneously for a semi-quantitative assay and purification of receptor, as the following example shows:

$GH_4C_1$ membranes (1.7 mg membrane protein/sample in triplicate) are incubated with increasing concentrations of biotinyl-S28 (+[$^{125}$I]Bio-S28 as a tracer). FIG. 10A shows that increasing amounts of B28 binds to the membranes until binding is at or near saturation (1.8 pMoles total specific binding) when 10 nM B28 is present in the binding step.

The membranes from each point in the binding curve (10 mg total membrane protein) are solubilized in 0.15% deoxycholate:lysolecithin and centrifuged at 100,000×g to remove insoluble material. Soluble material is adsorbed to streptavidin-Sepharose for 4 hours and eluted with 100 uM GTP-gamma-S+100 uM EDTA+100 uM EGTA. Then the GTP-gamma-S eluates are incubated overnight with immobilized wheat germ agglutinin (to adsorb glycoproteins, including the receptor).

The WGA-agarose pellets are washed and then boiled in SDS polyacrylamide gel sample buffer (to melt the agarose and solubilize proteins). The samples are applied to 12% polyacrylamide gels and separated by electrophoresis (FIG. 10B). The proteins not bound to WGA are processed separately and also separated by SDS-PAGE (FIG. 10C).

Staining of the gels shows that a glycoprotein of MW 75-95,000 is the only glycoprotein specifically bound to and eluted from streptavidin. The recovery of this protein parallels the initial binding curve. This shows ligand dependance. Ligand specificity is shown by the absence of the 75-95,000 MW glycoprotein when 10 nM B28 is competed out of the binding pocket by 10,000 nM non-biotinylated SRIF-14.

FIG. 10C shows the pattern for non-glycoproteins. It is clear that most of the proteins appear in all samples, i.e., are non-ligand dependent contaminants. However, a 40,000 MW protein (dot) appears in increasing amounts paralleling the binding curve and is also absent when B28 is competed out by non-biotinylated S14. This is independently shown to be the G-alpha-o G-protein subunit by two criteria: (a) ADP ribosylation with pertussis toxin (FIG. 8) and (b) immunoblotting with a specific antibody.

It is important to point out that the above adaptation of the purification method as a receptor assay serves very close to the same purpose as a ligand binding assay of purified material eluted from an affinity column. The standard for purity of a protein with a defined function is that the function exists in a preparation containing only one protein. Here, it is shown that only one glycoprotein (with appropriate size for the SRIF receptor) is purified in a ligand-specific and ligand concentration-dependent manner. Elution with GTP-gamma-S, an agent known to lower affinity of G protein-linked receptors, and the specific co-purification of a G protein subunit further reinforces the identify of the 75-95K glycoprotein as the SRIF receptor. We believe this adaptation of the purification protocol for the purpose of receptor identification can be widely used for other receptors. A key element of the method is that it is not necessary to develop binding assays for solubilized receptors. Rather, all receptor purification and identification is done with preformed receptor:ligand complexes.

What we claim is:

1. A method for purification of a receptor polypeptide comprising:
    (a) contacting a ligand capable of specifically binding the receptor with cell membranes containing the receptor to form a receptor:ligand complex;
    (b) solubilizing the receptor:ligand complex;
    (c) contacting the solubilized receptor:ligand complex with a solid phase substrate which binds the receptor:ligand complex by specifically binding with the ligand;
    (d) dissociating the receptor from the substrate bound receptor:ligand complex with an eluant capable of releasing the receptor from the receptor:ligand complex to produce an eluate containing a purified receptor.

2. The method of claim 1 in which the receptor's specific G protein remains associated with the receptor:ligand complex up to step (d), and in which the receptor and G protein are both contained in the eluate and by which elution yields both receptor and dissociated G protein.

3. The method of claim 1 which includes the further step of (e) recovering the receptor from the eluate.

4. The method of claim 3 in which the receptor is further purified by contact with a substrate capable of binding a glycoprotein.

5. The method of claim 1 in which the eluant is capable of separating the G protein from the receptor.

6. The method of claim 1 in which the receptor:ligand complex is solubilized with a bile salt-like detergent.

7. The method of claim 1 in which the ligand is biotinylated.

8. The method of claim 7 in which the substrate of step (c) contains avidin or streptavidin.

9. The method of claim 1 in which the eluant in step (d) contains a dication chelating agent.

10. The method of claim 9 in which the eluant contains EDTA, EGTA or a combination thereof.

11. The method of claim 5 in which the eluant contains a GTP analog.

12. The method of claim 10 in which the eluant also contains a GTP analog.

13. The method of claim 4 in which the receptor is further purified by lectin affinity chromatography.

14. A method for purification of a G protein-linked somatostatin receptor comprising:
    (a) contacting a biotinylated somatostatin analog ligand with cellular material containing the somatostatin receptor to form a receptor:ligand complex;
    (b) solubilizing the receptor:ligand complex in a bile salt-like detergent;
    (c) contacting the solubilized receptor:ligand complex with a substrate containing avidin or streptavidin; and
    (d) contacting the bound receptor:ligand complex with an eluant containing a dicationic chelating agent, or a GTP analog, or both to release the receptor into an eluate.

15. The method of claim 15 in which the ligand is bioS28 or bioS14.

16. The method of claim 14 in which the receptor is a pituitary somatostatin receptor.

17. The method of claim 14 in which the receptor:ligand complex is solubilized with deoxycholate.

18. The method of claim 17 in which the deoxycholate is combined with lysolecithin at a concentration of up to about 0.2%.

19. The method of claim 14 in which the eluant contains EDTA, EGTA and GTP-γ-S.

20. The method of claim 14 in which the receptor is further purified by binding with wheat germ agglutinin and elution with N-N'-N''-triacetylchitotriose.

* * * * *

UNITED STATES PATENT AND TRADEMARK OFFICE
CERTIFICATE OF CORRECTION

PATENT NO. : 5,225,543
DATED : July 6, 1993
INVENTOR(S) : Cecil M. Eppler et al

It is certified that error appears in the above-indentified patent and that said Letters Patent is hereby corrected as shown below:

Column 23, lines 14 and 15, "a receptor polypeptide comprising" should read --a G protein-linked receptor polypeptide comprising--.

Signed and Sealed this

Fourteenth Day of June, 1994

Attest:

BRUCE LEHMAN

*Attesting Officer*  *Commissioner of Patents and Trademarks*